US009222105B2

(12) United States Patent
Cost et al.

(10) Patent No.: US 9,222,105 B2
(45) Date of Patent: Dec. 29, 2015

(54) METHODS AND COMPOSITIONS FOR MODIFICATION OF THE HPRT LOCUS

(71) Applicants: Sangamo BioSciences, Inc., Richmond, CA (US); The Regents of the University of California, Oakland, CA (US)

(72) Inventors: Gregory J. Cost, Berkeley, CA (US); Michael C. Holmes, Oakland, CA (US); Noriyuki Kasahara, Oakland, CA (US); Josee Laganiere, El Cerrito, CA (US); Jeffrey C. Miller, San Leandro, CA (US); David Paschon, Oakland, CA (US); Edward J. Rebar, San Francisco, CA (US); Fyodor Urnov, Richmond, CA (US); Lei Zhang, Davis, CA (US)

(73) Assignees: Sangamo BioSciences, Inc., Richmond, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/660,821

(22) Filed: Oct. 25, 2012

(65) Prior Publication Data
US 2013/0137104 A1    May 30, 2013

Related U.S. Application Data

(60) Provisional application No. 61/552,309, filed on Oct. 27, 2011, provisional application No. 61/556,691, filed on Nov. 7, 2011.

(51) Int. Cl.
*C12N 9/22*      (2006.01)
*C12N 15/85*     (2006.01)
*C12N 9/96*      (2006.01)
*C12N 15/90*     (2006.01)
*C12N 9/10*      (2006.01)

(52) U.S. Cl.
CPC .............. *C12N 15/85* (2013.01); *C12N 9/1077* (2013.01); *C12N 9/22* (2013.01); *C12N 9/96* (2013.01); *C12N 15/907* (2013.01); *C12Y 204/02008* (2013.01); *C12Y 301/21004* (2013.01); *C07K 2319/81* (2013.01)

(58) Field of Classification Search
CPC combination set(s) only.
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas et al. | |
| 6,140,466 A | 10/2000 | Barbas et al. | |
| 6,200,759 B1 | 3/2001 | Dove et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 7,951,925 B2 | 5/2011 | Ando et al. | |
| 2003/0044404 A1 | 3/2003 | Rebar et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0245476 A1 | 11/2005 | Collingwood et al. | |

(Continued)

FOREIGN PATENT DOCUMENTS

GB      2338237      6/2011
WO      WO 95/19431  7/1995

(Continued)

OTHER PUBLICATIONS

CompoZr knockout ZFN kit, 2014; at www.sigmaaldrich.com/catalog/product/sigma/ckozfn33445?lang-en®ion=US.*

(Continued)

*Primary Examiner* — Karen Cochrane Carlson
(74) *Attorney, Agent, or Firm* — Dahna S. Pasternak; Pasternak Patent Law

(57) ABSTRACT

Nucleases and methods of using these nucleases for modification of an HPRT locus and for increasing the frequency of gene modification at a targeted locus and clones and for generating animals.

29 Claims, 16 Drawing Sheets

(56) References Cited

U.S. PATENT DOCUMENTS

| | | |
|---|---|---|
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2008/0188000 A1 | 8/2008 | Relk et al. |
| 2008/0299580 A1 | 12/2008 | DeKelver et al. |
| 2009/0068164 A1 | 3/2009 | Segal et al. |
| 2010/0047805 A1 | 2/2010 | Wang |
| 2010/0199389 A1 | 8/2010 | Butler et al. |
| 2010/0218264 A1 | 8/2010 | Cui et al. |
| 2011/0145940 A1 | 6/2011 | Voytas et al. |
| 2011/0158957 A1 | 6/2011 | Bonini |
| 2011/0201055 A1 | 8/2011 | Doyon et al. |
| 2011/0207221 A1 | 8/2011 | Cost et al. |
| 2011/0287512 A1 | 11/2011 | Paschon |
| 2011/0301073 A1 | 12/2011 | Gregory et al. |
| 2013/0171732 A1* | 7/2013 | Holmes et al. ............ 435/462 |

FOREIGN PATENT DOCUMENTS

| | | |
|---|---|---|
| WO | WO 96/06166 | 2/1996 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/27878 | 5/2000 |
| WO | WO 01/60970 | 8/2001 |
| WO | WO 01/88197 | 11/2001 |
| WO | WO 02/16536 | 2/2002 |
| WO | WO 02/077227 | 10/2002 |
| WO | WO 02/099084 | 12/2002 |
| WO | WO 03/016496 | 2/2003 |
| WO | 03080809 A2 | 10/2003 |
| WO | WO 2007/014275 | 2/2007 |
| WO | 2008059382 A2 | 5/2008 |
| WO | WO 2009/042163 | 2/2009 |
| WO | WO 2010/079430 | 7/2010 |
| WO | WO 2011/011767 A1 | 1/2011 |
| WO | 2013123408 A1 | 8/2013 |

OTHER PUBLICATIONS

Pelascini et al. 2014; Lentiviral Vectors Encoding Zinc-Finger Nucleases Specific for the Model Target Locus HPRT1 Gene Correction Methods in Molecular Biology vol. 1114, 2014, pp. 181-199, abstract only at http://link.springer.com/protocol/10.1007%2F978-1-62703-761-7_12.*

Mittelman et al. 2009; Zinc-finger directed double-stand breaks within CAG repeat tracts promote repeat instability in human cells. PNAS 106(24): 9607-9612.*

Beerli et al., "Engineering Polydactyl Zinc-Finger Transcription Factors," *Natl Biotechnol* 20:135-141 (2002).

Bitinaite et al., "FOK I Dimerization is Required for DNA Cleavage," *Proc Natl Acad Sci USA* 95(18):10570-10575 (1998).

Boch et al., "Breaking the Code of the DNA Binding Specificity of TAL-Type III Effectors," *Science* 326(5959):1509-1512 (2009).

Bonas et al., "Genetic and Structural Characterization of the Avirulence Gene AVRBS3 From Xanthomonas Campestris PV. Vesicatoria,"*Mol Gen Genet* 218(1):127-136 (1989).

Choo et al., "Advances in Zinc Finger Engineering," *Curr Opin Struct Biol* 10:411-416 (2000).

Dekelver et al., "Functional Genomics, Proteomics, and Regulatory DNA Analysis in Isogenic Settings Using Zinc Finger Nuclease-Driven Transgenesis Into a Safe Harbor Locus in the Human Genome," *Genome Research* 20(8):1133-1142 (2010).

Guschin et al., "A Rapid and General Assay for Monitoring Endogenous Gene Modification," *Methods Mol Biol* 649:247-256 (2010).

Heuer et al., "Repeat Domain Diversity of AVRBS3 Like Genes in Ralstonia Solanacearum Strains and Association With Host Preferences in the Field," *Appl Environ Microbiol* 73(13):4379-4384 (2007).

Isalan et al., "A Rapid Generally Applicable Method to Engineer Zinc Fingers Illustrated by Targeting the HIV-1 Promotor," *Nat Biotechnol* 19:656-660 (2001).

Jasin et al., "Targeted Transgenesis," *Proc Natl Acad Sci USA* 93(17):8804-8808 (1996).

Jena et al., "Redirecting T-Cell Specificity by Introducing a Tumor-Specific Chimeric Antigen Receptor," *Blood* 116(7):1035-1044 (2010).

Kay et al., "A Bacterial Effector Acts as a Plant Transcription Factor and Induces a Cell Size Regulator," *Science* 318(5850):648-651 (2007).

Kim et al., "Hybrid Restriction Enzymes: Zinc Finger Fusions to FOK I Cleavage Domain," *Proc Natl Acad Sci USA* 93(3):1156-1160 (1996).

Kim et al., "Insertion and Deletion Mutants of FOK I Restriction Endonuclease," *J Biol Chem* 269:31978-31982 (1994).

Li et al., "Alteration of the Cleavage Distance of FOK I Restriction Endonuclease by Insertion Mutagenesis," *Proc Natl Acad Sci USA* 90(7):2764-2768 (1993).

Li et al., "Functional Domains in FOK I Restriction Endonuclease," *Proc Natl Acad Sci USA* 89(10):4275-4279 (1992).

Meek et al., "Efficient Gene Targeting by Homologous Recombination in Rat Embryonic Stem Cells," *PLoS One* 5:e14225 (2010).

Pabo et al., "Design and Selection of Novel CYS2HIS2 Zinc Finger Proteins," *Annu Rev Biochem* 70:313-340 (2001).

Perez et al., "Establishment of HIV-1 Resistance in CD4+ T Cells by Genome Editing Using Zinc-Finger Nucleases," *Nat Biotechnol* 26(7):808-816 (2008).

Porter et al., "Interfering RNA-Mediated Purine Analog Resistance for in Vitro and in Vivo Cell Selection," *Blood* 112:4466-4474 (2008).

Schornack et al., "Gene for Gene Mediated Recognition of Nuclear Targeted AVRBS3 Like Bacterial Effector Proteins," *J Plant Physiol* 163(3):256-272 (2006).

UniProtKB Accession No. F7BA68_CIOIN (2011).

Urnov et al., "Highly Efficient Endogenous Human Gene Correction Using Designed Zinc-Finger Nucleases," *Nature* 435(7042):646-651 (2005).

Yang el al., "Purification, Cloning, and Characterization of the CEL I Nuclease," *Biochemistry* 39, 3533-3541 (2000).

Monnat, et al., "Nucleotide Sequence Analysis of Human Hypdxanthine Phosphoribosyltransferase (HPRT) Gene Deletions," *Genomics* 1:777-787 (1992).

Suzuki, et al., "Development of Zinc-Finger Nucleases Targetting the Human HRPT Locus," *Journal of Gene Medicine* 12(12):1063 (2010).

* cited by examiner

METHODS AND COMPOSITIONS FOR MODIFICATION OF THE HPRT LOCUS

CROSS-REFERENCE TO RELATED APPLICATIONS

This application claims the benefit of the following U.S. Provisional Patent application Nos. Appl. No. 61/552,309, filed Oct. 27, 2011 and U.S. Prov. Appl. No. 61/556,691, filed Nov. 7, 2011; the disclosures of which are incorporated by reference in their entireties for all purposes.

TECHNICAL FIELD

The present disclosure is in the fields of genome editing.

BACKGROUND

Gene therapy holds enormous potential for a new era of human therapeutics. These methodologies will allow treatment for conditions that heretofore have not been addressable by standard medical practice. Gene therapy can include the many variations of genome editing techniques such as disruption or correction of a gene locus, and insertion of an expressible transgene that can be controlled either by a specific exogenous promoter fused to the transgene, or by the endogenous promoter found at the site of insertion into the genome.

Delivery and insertion of the transgene are examples of hurdles that must be solved to implement this technology. For example, although a variety of gene delivery methods are potentially available for therapeutic use, all involve substantial tradeoffs between safety, durability and level of expression. Methods that provide the transgene as an episome (e.g. basic adenovirus, AAV and plasmid-based systems) are generally safe and can yield high initial expression levels, however these methods lack robust episome replication which may limit the duration of expression in mitotically active tissues or those that regenerate over time. In contrast, delivery methods that result in the random integration of the desired transgene (e.g. integrating lentivirus) provide more durable expression but might provoke unregulated growth in the recipient cells, potentially leading to malignancy via activation of oncogenes in the vicinity of the randomly integrated transgene cassette. Moreover, although transgene integration avoids replication-driven loss, it does not prevent eventual silencing of the exogenous promoter fused to the transgene. Over time, such silencing results in reduced transgene expression for the majority of random insertion events. Integration of a transgene rarely occurs in every target cell, which can make it difficult to attain a high enough level of transgene expression to achieve the desired therapeutic effect.

In recent years, a new strategy for transgene integration has been developed that uses cleavage with site-specific nucleases to bias insertion into a chosen genomic locus (see, e.g. co-owned U.S. Pat. No. 7,888,121 and U.S. Patent Publication No. 20110301073). This approach offers the prospect of improved transgene expression, increased safety and expressional durability, as compared to classic integration approaches, since it allows exact transgene positioning at a minimal risk of gene silencing or activation of nearby oncogenes.

One approach involves the integration of a transgene into its cognate locus, for example, insertion of a wild type factor VIII transgene into the endogenous factor VIII locus to correct a mutant gene. Alternatively, the transgene may be inserted into a non-cognate locus chosen specifically for its beneficial properties. Targeting the cognate locus can be useful if one wishes to replace expression of the endogenous gene with the transgene while still maintaining the expressional control exerted by the endogenous regulatory elements. Specific nucleases can be used that cleave within or near the endogenous locus and the transgene can be integrated at or near the site of cleavage through homology directed repair (HDR) or by end capture during non-homologous end joining (NHEJ). The integration process is influenced by the use or non-use of regions of homology on the transgene donors. These regions of chromosomal homology on the donor flank the transgene cassette and are homologous to the sequence of the endogenous locus at the site of cleavage.

Alternatively, the transgene may be inserted into a specific "safe harbor" location in the genome that may either utilize the promoter found at that safe harbor locus, or allow the expressional regulation of the transgene by an exogenous promoter that is fused to the transgene prior to insertion. Several such "safe harbor" loci have been described, including the AAVS1 (also known as PPP1R12C) and CCR5 genes in human cells, Rosa26 and albumin (see co-owned U.S. Patent Publication Nos. 20080299580, 20080159996 and 201000218264 and U.S. application Ser. Nos. 13/624,193 and 13/624,217). As described above, nucleases specific for the safe harbor can be utilized such that the transgene construct is inserted by either HDR- or NHEJ-driven processes.

6-thioguanine (6-TG) is a guanine analog that can interfere with dGTP biosynthesis in the cell. Thio-dG can be incorporated into DNA during replication in place of guanine, and when incorporated, often becomes methylated. This methylation can interfere with proper mis-match DNA repair and can result in cell cycle arrest, and/or initiate apoptosis. 6-TG has been used clinically to treat patients with certain types of malignancies due to its toxicity to rapidly dividing cells.

Treatment of some types of medical conditions, such as cancers, autoimmune diseases and the like often involves an immunoablation to remove the patient's own immune system, for example, prior to transplant of a bone marrow or other tissue graft Immunoablation can be accomplished by total body radiation or by high dose chemotherapy. Although such treatment is thought to "reboot" the immune system by allowing the graft to take hold in the patient, the immunoablation treatment is often harsh and not well tolerated by the patient and can lead to severe complications depending on the treatment regime utilized. Thus, there is a need for a milder regiment for immunoablative therapy.

Hypoxanthine-guanine phosphoribosyltransferase (HPRT) is an enzyme involved in purine metabolism encoded by the HPRT1 gene. HPRT1 is located on the X chromosome, and thus is present in single copy in males. HPRT1 encodes the transferase that catalyzes the conversion of hypoxanthine to inosine monophosphate and guanine to guanosine monophosphate by transferring the 5-phosphorobosyl group from 5-phosphoribosyl 1-pyrophosphate to the purine. The enzyme functions primarily to salvage purines from degraded DNA for use in renewed purine synthesis. In the presence of 6-TG, HPRT is the enzyme responsible for the integration of 6-TG into DNA and RNA in the cell, resulting in blockage of proper polynucleotide synthesis and metabolism. Thus, 6-TG can be used as a selection agent to kill cells with a functional HPRT enzyme, and in addition, 6-TG can be given to cause mild immunoablation in subjects in need thereof. In a patient receiving a stem cell graft (e.g. hematopoietic or progenitor stem cells), a transgene of interest can be integrated into the HPRT locus, knocking out the HPRT1 gene. Such a cell population will be resistant to 6-TG toxicity. Thus when the transgene (+)/HPRT1 (−) cells are infused into the patient, a mild course of 6-TG may increase engraftment of the cells, and those cells that engraft will have a greater percentage of transgene integration.

HPRT has been targeted traditionally as a safe harbor for transgene integration (see for example Jasin et al (1996) *Proc Natl Acad Sci USA* 93, p. 8804). It is constitutively expressed at a low level, and disruption of the HPRT gene can be selected for both in vitro and in vivo using 6-TG. However, integration into an HPRT locus via random integration can be difficult and occurs only at a low frequency.

Thus, there remains a need for compositions and methods to increase the frequency of specific genome editing by directly targeting the HPRT gene, or by using targeted disruption of this gene as a marker both for the successful transduction of nucleic acids into a cell (at the HPRT or other loci) and as a marker for expression and function of the transfected nuclease(s).

SUMMARY

Disclosed herein are methods and compositions for increasing targeted insertion of a transgene into a specific location within the cell or increasing the frequency of gene modification in a targeted locus. In some embodiments, transgene insertion occurs at the HPRT gene, and selection of transgene insertion occurs by using exposure of the cell, animal, or patient to 6-TG. In other embodiments, disruption of the HPRT gene by nuclease cleavage (e.g., gene knockout due to nucleotide insertion or deletion during NHEJ following cleavage) serves as a proxy for cells with active nuclease activity, and transgene insertion occurs at one or more other locations within the genome in the presence of an additional nuclease co-transduced with the donor transgene and the HPRT-specific nuclease. Insertion can occur at any locus, including, for example, a safe harbor location, such as AAVS1, Rosa, Albumin or CCR5, or at the endogenous location of any gene of interest. Insertion of a transgene into a corresponding endogenous locus can be for gene knock out, gene correction, or for the introduction of gene variants with desired attributes or for the introduction of a gene encoding a polypeptide or polynucleotide of interest.

In some embodiments, two or more sets of nucleases, where one set targets HPRT and the other targets another location of interest, are introduced (simultaneously and/or sequentially in any order) into the cell, such that knock out of both loci occurs through NHEJ-mediated repair of the double strand breaks (DSB) induced by cleavage by the nuclease sets. In these embodiments, nuclease-mediated HPRT disruption is used as a marker for successful transduction of the nuclease pairs, as well as for an indicator of cells containing nuclease activity. This is useful for increasing the efficiency of identification of cells in which genome editing has likely occurred. In some embodiments, the methods and compositions are used in T or B cells, and in others, they are used in stem cells, for example hematopoietic stem cells (e.g., CD34+ cells). In some embodiments, the methods and compositions of the invention are used with hematopoietic stem/progenitor cells.

In one aspect, described herein is a zinc-finger protein (ZFP) that binds to target site in an HPRT gene in a genome, wherein the ZFP comprises one or more engineered zinc-finger binding domains. In one embodiment, ZFPs are used as a pair of zinc-finger nucleases (ZFNs) that dimerize and then cleave a target genomic region of interest, wherein the ZFNs comprise one or more engineered zinc-finger binding domains and a nuclease domain or cleavage half-domain. In another aspect, described herein is a TALE protein (Transcription activator like effector) that binds to target site in an HPRT gene in a genome, wherein the TALE comprises one or more engineered TALE DNA binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains of ZFNs and/or TALENs can be obtained, for example, from various restriction endonucleases and/or homing endonucleases. In one embodiment, the cleavage half-domains are derived from a Type IIS restriction endonuclease (e.g., Fok I). In certain embodiments, the zinc finger or TALE DNA binding domain recognizes a target site in an HPRT gene, for example as shown in Tables 1 and 4.

The ZFN or TALEN may bind to and/or cleave an HPRT gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein are compositions comprising one or more of the zinc-finger or TALE nucleases described herein. In certain embodiments, the composition comprises one or more zinc-finger or TALE nucleases in combination with a pharmaceutically acceptable excipient. In some embodiments, the composition comprises two or more sets of zinc finger or TALE nucleases, each set with different specificities. In some aspects, one set of the zinc-finger or TALE nucleases is specific for an HPRT gene. In other aspects, the composition comprises both ZFNs and TALENs. In some embodiments, the composition comprises polynucleotides encoding HPRT-specific nucleases, while in other embodiments, the composition comprises nuclease proteins.

In another aspect, described herein is a polynucleotide encoding one or more ZFNs or TALENs described herein. The polynucleotide may be, for example, mRNA or DNA. In some aspects, the mRNA may be chemically modified (See e.g. Kormann et al, (2011) *Nature Biotechnology* 29(2):154-157). In another aspect, described herein is a ZFN or TALEN expression vector comprising a polynucleotide, encoding one or more ZFNs or TALENs described herein, operably linked to a promoter. In one embodiment, the expression vector is a viral vector. In one aspect, the viral vector exhibits tissue specific tropism.

In another aspect, described herein is a host cell comprising one or more ZFN or TALEN expression vectors. The host cell may be stably transformed or transiently transfected or a combination thereof with one or more ZFN or TALEN expression vectors. In one embodiment, the host cell is an embryonic stem cell. In other embodiments, the one or more ZFN or TALEN expression vectors express one or more ZFNs or TALENs in the host cell. In another embodiment, the host cell may further comprise an exogenous polynucleotide donor sequence. In any of the embodiments, described herein, the host cell can comprise an embryo cell, for example a one or more mouse, rat, rabbit or other mammal cell embryo (e.g., a non-human primate). In some embodiments, the host cell comprises a tissue.

In another aspect, described herein is a method for cleaving an HPRT gene in a cell, the method comprising: (a) introducing, into the cell, one or more polynucleotides encoding one or more ZFNs or TALENs that bind to a target site in the one or more genes under conditions such that the ZFN(s) is (are) or TALENs is (are) expressed and the one or more HPRT genes are cleaved. Co-transduction of both sets is performed and then the recipient cells can be selected using 6-TG. In other embodiments, cells resistant to 6-TG through a knockout of HPRT by NHEJ following the nuclease-induced DSB can also be modified via nuclease-mediated cleavage at a different (non-HPRT) site, for example via cleavage by the second nuclease set followed by NHEJ. Examples of genes that may be knocked out by this protocol include the HIV co-receptors CCR5 or CXCR4.

In other embodiments, a genomic sequence in the target gene is cleaved, for example using a ZFN or TALEN (or vector encoding said ZFN or TALEN) as described herein and a "donor" sequence inserted into the gene following targeted cleavage with the ZFN or TALEN. The donor sequence may be present in the ZFN or TALEN vector, present in a separate vector (e.g., Ad, AAV or LV vector) or, alternatively, may be introduced into the cell using a separate and/or different nucleic acid delivery mechanism. Insertion of a donor nucleotide sequence into the HPRT locus can result in the expression of the transgene under control of the HPRT genetic control elements. In some aspects, insertion of the transgene of interest results in expression of an intact exogenous protein sequence and lacks any HPRT-encoded amino acids. In other aspects, the expressed exogenous protein is a fusion protein and comprises amino acids encoded by the transgene and by the HPRT gene. In some instances, the HPRT sequences will be present on the amino (N)-terminal portion of the exogenous protein, while in others, the HPRT sequences will be present on the carboxy (C)-terminal portion of the exogenous protein. In other instances, HPRT sequences will be present on both the N- and C-terminal portions of the exogenous protein.

In some embodiments, the invention describes methods and compositions that can be used to express a transgene under the control of the HPRT promoter in vivo. In some aspects, the transgene may encode a therapeutic protein of interest. The transgene may encode a protein such that the methods of the invention can be used for protein replacement. In some aspects, the transgenes are inserted into B cells for production of the protein encoded by the transgene for export into the blood. Other non-limiting examples include treatment of hemoglobinopathies in CD34+ stem/progenitor cells by introduction of wild-type or anti-sickling globin sequences in patients with aberrant globin genes. In some aspects, the transgenes encode therapeutic proteins, therapeutic hormones, plasma proteins, antibodies and the like. Another non-limiting example includes the insertion of a chimeric antigen receptor (CAR) or insertion of one or more T cell receptor gene(s) into a T cell ex vivo for reinfusion into a patient in need thereof (See Jena et al (2010) *Blood* 116: 1035-1044). In further aspects, the methods and compositions of the invention are used to knock out a gene in a cell. A non-limiting example includes the knock out of a viral receptor such as CCR5 in T cells ex vivo for reinfusion into a patient in need thereof. Treatment of hemoglobinopathy by knockout of the Bcl11A gene or EKLF gene, or by knocking out the EKLF binding site in the Bcl11A gene, all which will result in a reactivation of fetal (γ) globin synthesis, are other non-limiting examples. Other embodiments include the knockout of HLA genes or gene correction of a gene or insertion of splice acceptor sites.

In some embodiments, the ZFN or TALEN cleavage site is in an intron of the HPRT gene such that repair of the ZFN- or TALEN-induced DSB using NHEJ will produce a cell that remains sensitive to 6-TG. In some embodiments, the DNA integrated into HPRT contains a splice acceptor sequence to disrupt normal splicing of HPRT wherein disruption of HPRT splicing inactivates the gene, creating 6-TG resistant cells. In some embodiments, the integrated DNA contains a transgene that uses the captured splice-form to produce a fusion protein with HPRT. In other embodiments, the integrated DNA comprises a promoter and a transgene such that HPRT splicing is disrupted and the transgene is expressed.

In other embodiments, disruption of the HPRT gene by nuclease cleavage, (e.g., gene knockout due to nucleotide insertion or deletion during NHEJ) serves as a marker for positive transduction and active nuclease activity, and transgene insertion can occur at another location within the genome (e.g. a safe harbor). Such methods of enriching for nuclease-modified cells and compositions can be used to enrich for modifications at a locus other than HPRT, for example inactivation of and/or integration of a transgene at a non-HPRT locus. The transgene may be under the control of another endogenous or exogenous promoter of interest in vivo or in vitro. In some aspects, the transgene may encode a protein of interest, for example a therapeutic or replacement protein (e.g., hormones, plasma proteins, antibodies, etc.) Non-limiting examples of transgenes encoding protein therapeutics or replacements include sequences encoding wild type globin proteins (e.g., in CD34+ stem cells for the treatment of hemoglobinopathies in patients with aberrant globin genes); a chimeric antigen receptor (CAR) and/or T-cell receptor gene(s) (e.g., ex vivo insertion in a T cell for reinfusion into a patient in need thereof); clotting factors (e.g., for the treatment of subjects with clotting disorders, for example via ex vivo or in vivo targeted insertion hematopoietic cells or CD34+ hematopoietic stem cells, hepatocytes or hepatic stem cells); and/or one or more anti-HIV proteins, and insertion of wild type copies of aberrant genes for correction or prevention of a disease (e.g. treatment of a lysosomal storage disease).

In further aspects, the methods and compositions of the invention are used to monitor knock out of a gene in a cell. A non-limiting example includes monitoring the nuclease-mediated knock out of a viral receptor such as CCR5 in T cells ex vivo for reinfusion into a patient in need thereof. Other embodiments include gene correction of a gene or insertion of splice acceptor sites. In these embodiments, the HPRT knock out as described herein, followed by exposure of the cells to 6-TG in vivo or in vitro selects cells in which transduction of the nuclease-mediated targeted modification (e.g., inactivation or insertion) at a locus other than HPRT has been successful due to nuclease activity.

In some embodiments, the methods of the invention may be used in vivo in the development of transgenic animal systems. In some aspects, the transgenic animal may be used in model development where the transgene encodes a human gene. In some instances, the transgenic animal may be knocked out at the corresponding endogenous locus, allowing the development of an in vivo system where the human protein may be studied in isolation. Such transgenic models may be used for screening purposes to identify small molecules, large biomolecules or other entities which may interact or modify the human protein of interest. In other aspects, the transgenic animals may be used for production purposes, for example, to produce antibodies or other biomolecules of interest. In certain embodiments, the animal is a small mammal, for example a rabbit or a rodent such as rat, a mouse or a guinea pig. In other embodiments, the animal is a non-human primate. In yet further embodiments, the animal is a farm animal such as a cow, goat or pig. In some aspects, the transgene is integrated into the HPRT locus in an embryonic stem cell or animal embryo by any of the methods described herein, and then the embryo is implanted such that a live animal is born. The animal is then raised to sexual maturity and allowed to produce offspring wherein at least some of the offspring comprise the integrated transgene.

In a still further aspect, provided herein is a method for site specific integration of a nucleic acid sequence into an HPRT locus of a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger or TALE nuclease that recognizes the site of integration in the HPRT locus, and (b) culturing the embryo to allow expression of the zinc finger or TALE nuclease, wherein a double stranded break introduced into the site of integration by the zinc finger nuclease or TALEN is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a zinc finger or TALE nuclease. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

In any of the methods or compositions described herein, the cell containing the engineered HPRT locus or other genomic editing can be a stem or progenitor cell. Specific stem cell types that may be used with the methods and compositions of the invention include embryonic stem cells (ESC), induced pluripotent stem cells (iPSC) and hematopoietic stem cells (e.g., CD34+ cells). The iPSCs can be derived from patient samples and from normal controls wherein the patient derived iPSC can be mutated to the normal or wild type gene sequence at the gene of interest, or normal cells can be altered to the known disease allele at the gene of interest. Similarly, the hematopoietic stem cells can be isolated from a patient or from a donor. These cells are then engineered to express the transgene or gene modification of interest, expanded and then reintroduced into the patient.

In any of the methods described herein, the polynucleotide encoding the zinc finger nuclease(s) or TALEN(s) can comprise DNA, RNA or combinations thereof. In certain embodiments, the polynucleotide comprises a plasmid. In other embodiments, the polynucleotide encoding the nuclease comprises mRNA.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided.

In another aspect, the methods and compositions of the invention provide for the use of cells, cell lines and animals (e.g., transgenic animals) in the screening of drug libraries and/or other therapeutic compositions (i.e., antibodies, structural. RNAs, etc.) for use in treatment of a hemoglobinopathy, lysosomal storage disease, musculoskeletal disease, a clotting disorder, cancer, HIV or the like. Such screens can begin at the cellular level with manipulated cell lines or primary cells, and can progress up to the level of treatment of a whole animal (e.g., human).

A kit, comprising the ZFPs or TALENs of the invention, is also provided. The kit may comprise nucleic acids encoding the ZFPs or TALENs, (e.g. RNA molecules or ZFP or TALEN encoding genes contained in a suitable expression vector), donor molecules, suitable host cell lines, instructions for performing the methods of the invention, and the like.

These and other aspects will be readily apparent to the skilled artisan in light of the disclosure as a whole.

BRIEF DESCRIPTION OF THE DRAWINGS

FIG. 5A demonstrates that the transgene was integrated via homologous recombination of the donor which was enriched 2-3 fold by 6-TG selection as measured in a semi-quantitative PCR based assay. FIG. 5B depicts an illustration showing the location of the 3 PCR primers used for the amplification in the assay, showing that the integration causes a larger PCR product to be produced (indicated by arrow in 5A) from the pgkr1+15512f primer pair while the HPRT r1−16078+15512f primer pair generates a shorter band from the unmodified locus. The use of the common forward primer 15512f and the generation of both wild type and integration specific bands allowed the PCR reaction to be used as a semi-quantitative assessment of the efficiency of targeted integration.

FIG. 8A depicts results of a Cel-I assay where the HPRT locus from nuclease treated cells was PCR amplified and then subjected to the Cel-I assay. Triangles over the sets indicate increasing amounts of TALEN expression plasmids used in the transfection. FIG. 8B depicts the amount of genome modification (% indels) as determined by the Cel-I assay.

FIG. 14A shows a schematic of the integrated transgene and illustrates where sequence will be deleted upon splicing. FIG. 14B depicts the percent of cells containing the GFP transgene in each of the conditions tested, with (right bars) and without (left bars) 6-TG selection. FIG. 14C is a graph showing cell viability in each of the conditions (left bars show with no selection and right bars shows with 6-TG selection.

FIG. 15A is a schematic of the integrated transgene and includes the location of the PCR primers used for amplification. FIG. 15B depicts a gel showing the PCR products and demonstrates targeted integration of the GFP transgene through targeted insertion (GFP TI) in the absence of selection.

DETAILED DESCRIPTION

Figure 1:
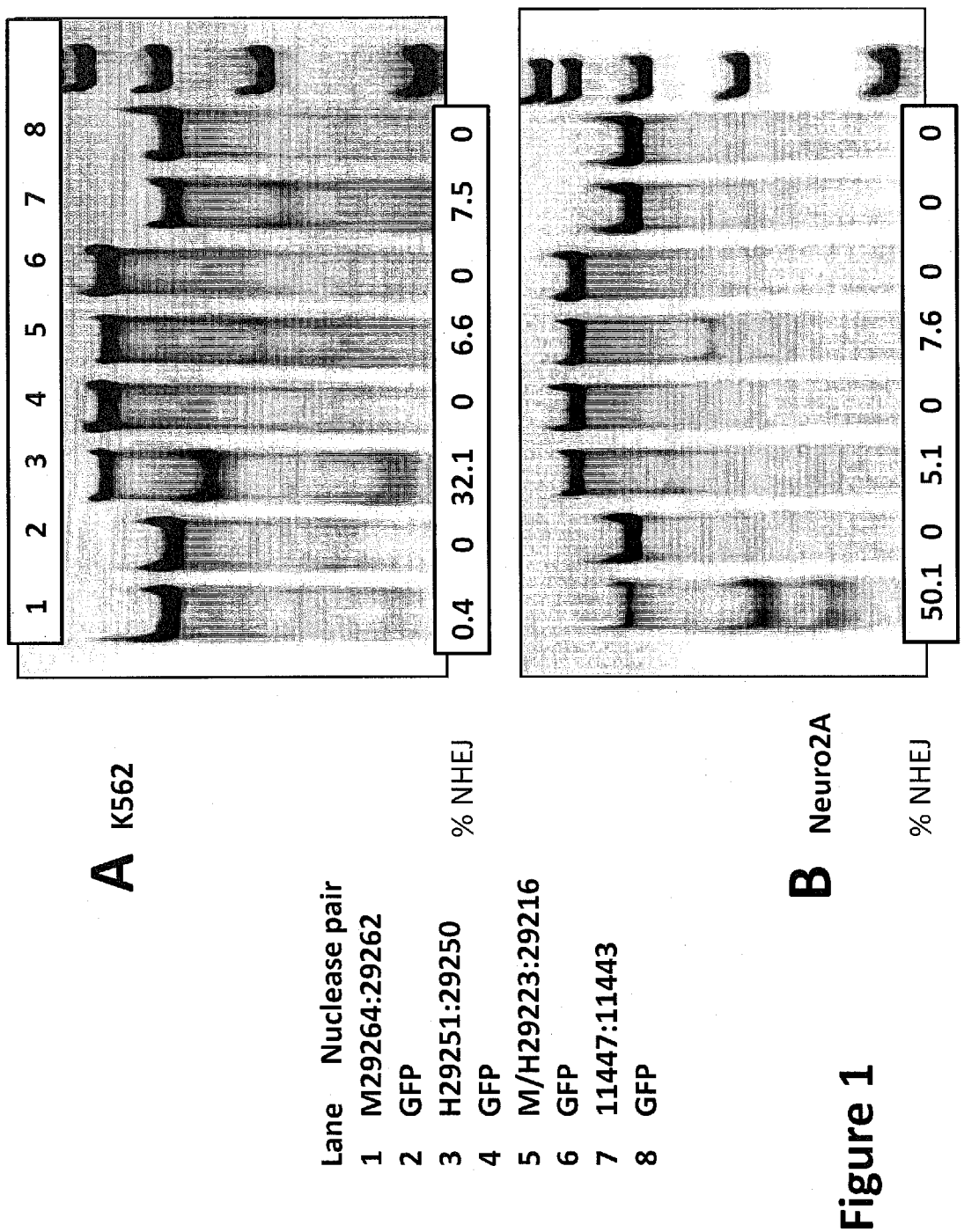
FIG. 1, panels A and B, depict gels demonstrating the results of a Cel-I mismatch assay (Surveyor™, Transgenomic) that measures cleavage at a location of interest by a set of zinc finger nuclease pairs that has been followed by an NHEJ event. NHEJ causes the insertion or deletion of nucleotide bases ("indels") which then creates a mismatch when the DNA strand is annealed with a wild type DNA strand. The Cel-I enzyme then cleaves the DNA at the site of this mismatch, creating two smaller fragments. The figure shows results after transfection of HPRT zinc finger nuclease pairs into K562 cells (FIG. 1A) or murine Neuro2A cells (FIG. 1B). The percent mismatch, or "% NHEJ", corresponds to the percentage of modified alleles and is a measure of the nuclease activity of each pair, and is indicated at the bottom of each lane. GFP are control cells that have been transfected with a GFP encoding plasmid.

Disclosed herein are methods and compositions for increasing insertion of a transgene into a specific location within the cell or increasing the frequency of gene editing or modification of a targeted locus. In some embodiments, the genome editing involves insertion of an exogenous transgene at an HPRT locus (e.g., HPTR1), and selection of transgene insertion occurs by exposure of the cell or animal to 6-TG. In other embodiments, disruption of an HPRT gene by nuclease cleavage (e.g., cleavage followed by gene knockout due to nucleotide insertion or deletion during NHEJ) serves as a marker for active nuclease activity, for example transgene insertion, at one or more other (non-HPRT) loci, In other embodiments, introduction of a nuclease pair targeting HPRT and a separate nuclease pair targeting a separate locus of interest results in gene knockout in both locations by NHEJ mediated double strand break repair.

Thus, the methods and compositions of the invention can be used to increase the efficiency of genome editing in a desired setting through the use of HPRT knockout, either by gene knock out, or by targeted insertion of a transgene into HPRT, followed in either instance by 6-TG selection. For example, the compositions and methods described herein can be used to insert a transgene that encodes and/or expresses a therapeutically beneficial protein (e.g., proteins such as globins or other involved in blood disorders such as clotting, anti-HIV proteins, CARs, T-cell receptor genes and a variety of other proteins, including monogenic proteins). Alternatively, these methods can be used to knockout another gene for therapeutic benefit or otherwise (e.g., knocking out of a repressor is beneficial if the gene product from the repressor gene is suppressing a gene whose product is needed).

Any of the compositions and methods described herein can be used for gene knock out and/or transgene insertion in any host cell. In certain embodiments, the cells are patient derived cells, e.g. patient derived induced pluripotent stem cells (iPSCs) or other types of stems or progenitor cells (embryonic, hematopoietic, neural, or mesenchymal as a non-limiting set). These altered stem cells can be hematopoietic or progenitor stem cells, for example, which can then be used in a bone marrow transplant. Alternatively, gene knock out and/or transgene integration can be accomplished in patient derived cells such as T cells ex vivo wherein the modified cells can then be reintroduced into the patient. Non-limiting examples of desirable loci for modification include viral receptors such as CD4, CCR5 or CXCR4.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, also, U.S. Patent Publication No. 20110301073.

Zinc finger binding domains can be "engineered" to bind to a predetermined nucleotide sequence, for example via engineering (altering one or more amino acids) of the recognition helix region of a naturally occurring zinc finger protein. Similarly, TALEs can be "engineered" to bind to a predetermined nucleotide sequence, for example by engineering of the amino acids involved in DNA binding (the "Repeat Variable Diresidue" or "RVD" region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Pat. No. 8,586,526.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084 and U.S. Pat. No. 8,586,526.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger and/or additional TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by deletion of sequences and/or by targeted integration of a donor sequence that disrupts expression of the gene(s) of interest. Cell lines with partially or completely inactivated genes are also provided.

Furthermore, the methods of targeted integration as described herein can also be used to integrate one or more exogenous sequences (also referred to as "donors" or "transgenes"). The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain) See, also, U.S. Patent Publication Nos. 20050064474, 20070218528, 20080131962, and 20110201055 incorporated herein by reference in their entireties.

The term "sequence" refers to a nucleotide sequence of any length, which can be DNA or RNA; can be linear, circular or branched and can be either single-stranded or double stranded. The terms "transgene" and "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more cleavage domain or other functional domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues may be thought of as individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to functional domain (e.g., cleavage domain, activation domain, repression domain, etc.), the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Nucleases

Described herein are compositions, particularly nucleases, which are useful targeting a gene for the insertion of a transgene, for example, nucleases that are specific for HPRT. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG family ("LAGLIDADG" disclosed as SEQ ID NO: 165), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-PpoI, I-SceIII, I-CreI, I-TevI, I-TevII and I-TevIII are known. See also U.S. Pat. No. 5,420,032; U.S. Pat. No. 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) 1 Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 201103073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schomack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site a HPRT gene is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and Ralstonia (see Heuer et al (2007) *Applied and Environmental Microbiology* 73(13): 4379-4384); U.S. Patent Publication Nos. 20110301073 and 20110145940.

In certain embodiments, the DNA binding domain that binds to a target site a HPRT gene comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789, 538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The zinc finger proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) Proc Nat'l Acad Sci USA 93(3):1156-1160. TALE proteins can also be fused to nuclease domains to create site-specific TALE nucleases (TALENs). ZFNs and TALENs have been used for genome modification in a variety of organisms. See, for example, United States Patent Publications 20030232410; 20050208489; 20050026157; 20050064474; 20060188987; 20060063231; 20110301073 and International Publication WO 07/014,275.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. See, also, U.S. Patent Publication Nos. 20050064474, 20070218528, 20080131962, and 20110201055

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Publication No. 20110201055). In still further embodiments, the engineered cleavage half domains comprise mutations such that a nuclease pair is made with one H537R-R487D-N496D ("RDD") FokI half domain and one N496D-D483R-H537R ("DRR") FoId half domain. See, e.g., U.S. Patent Publication No. 20110201055.

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice in a locus, for example an HPRT gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474; 20060188987 and 20110301073, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Provisional Patent Publication No. 20110287512.

Donors

As noted above, insertion of an exogenous sequence (also called a "donor sequence" or "donor" or "transgene"), for example for correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA and can be single-stranded or double-stranded and can be introduced into a cell in linear or circular form. See, e.g., U.S. Patent Publication Nos. 20100047805 and 20110207221. In addition, a donor polynucleotide may be a single or double stranded oligonucleotide. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. See, also, U.S. Patent Publication No. 20110207221.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or a macromolecule such as a dendrimir (See Wijagkanalen et al (2011) *Pharm Res* 28(7) p. 1500-19), or can be delivered by viruses (e.g., adenovirus, helper-dependent adenovirus, AAV, herpesvirus, retrovirus, lentivirus and integrase defective lentivirus (IDLV)).

The donor may be inserted so that its expression is driven by the endogenous promoter at the integration site, for example the promoter that drives expression of the HPRT gene. However, the donor may comprise a promoter and/or enhancer, for example a constitutive promoter or an inducible or tissue specific promoter.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503, 717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, helper-dependent adenovirus, poxvirus vectors; herpesvirus vectors and adeno-associated virus vectors, etc. See, also, U.S. Pat. Nos. 6,534,261; 6,607,882; 6,824, 978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, dendrimers, polycation or lipid:nucleic acid conjugates, naked DNA, artificial virions, agent-enhanced uptake of DNA or use of macromolecules such as dendrimers (see Wijagkanalen et al (2011) *Pharm Res* 28(7) p. 1500-19). Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946, 787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long teen expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Vivol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Any other AAV serotypes, including AAV1, AAV3, AAV4, AAV5, AAV6, AAV8, AAV9 and AAVrh10 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem/progenitor cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA complexed/formulated with a delivery vehicle (e.g. liposome or poloxamer) can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors or integrase defective lentivirus (IDLV). See, for example, Ory et al. (1996) *Proc. Natl. Acad. Sci. USA* 93:11382-11388; Dull et al. (1998) *J. Vivol.* 72:8463-8471; Zuffery et al. (1998) *J. Vivol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

APPLICATIONS

The methods and compositions of the invention can be used in any circumstance wherein it is desired to perform genome editing in a cell. Editing can be in the form of knocking out a desired gene or locus, or can encompass the targeted integration of a nucleic acid encoding a therapeutic transgene or structural nucleic acid such as an shRNA. The methods and compositions of the invention can be used to select for a targeted integration into the HPRT locus and/or to select for nuclease-mediated modification (e.g., insertion, deletion, inactivation) at another locus, such as a specific gene or safe harbor, for example, or the knockout of HPRT can be used as a marker for introduction of expression vector(s) encoding engineered nucleases (transduction) and a marker for successful nuclease activity. A desired transgene can be introduced directly into the HPRT locus, and the practitioner may select for integration by exposing the recipient cells to 6-TG. Alternatively, nucleases targeting HPRT may be introduced into a cell with another set of one or more engineered nucleases such that successful cleavage and knockout of HPRT may be used as a screen for cells with successful cleavage at the one or more additional targeted (non-HPRT) loci. Similarly, donors for targeted integration may be also introduced via one or more nucleases, and knockout of HPRT may be used as a screen for cells with successful nuclease activity, such that a pool of cells enriched for cleavage is identified, increasing the likelihood of cleavage at the alternative (non-HPRT) location(s). Knockout of a specific gene or locus is advantageous for many different technologies. One or more genes of interest may be knocked out in cell or animal models to study the phenotypic or other effects. Other genome editing approaches such as introduction of specific donor DNAs at specific locations can also be used in cell and animal models.

Modified cells may be used therapeutically, containing knock outs of specific genes such as virus receptors and co-receptors (e.g. CCR5), or regulatory genes and their products (Bcl11A, EKLF), aberrant genes (globin, blood factors, genes involved in lysosomal storage diseases), specific nucleic acid targets (EKLF binding site), self markers (HLA genes and their regulators), receptors such as endogenous T-cell receptors, to name a few. Knockout can be done with cells removed from a patient in need where the cells are treated ex vivo (e.g. T or B cells), and then reintroduced back via infusion, or they may be kept and expanded into a universal donor line. Stem or progenitor cells may be removed and treated ex vivo and also given to a patient in need thereof, for example modified hematopoietic (CD34+) stem cells. Patient specific and modified iPSC can also be made and used for patient treatment. Additionally, knockout may be done in vivo using introduction of the engineered nucleases via any suitable delivery method, for example AAVS or adenoviral vectors.

Donor integration also has a great many applications. Similar to the uses mentioned above for knockouts, targeted integration can be used to add gene(s) of interest at a desired location(s) including gene correction at an endogenous gene and addition of a DNA cassette to a safe harbor. Donor molecules may encode gene products such as therapeutic proteins or structural nucleic acids (e.g. shRNA). Uses for donors can include the addition of therapeutic products such as natural proteins, engineered antibodies, chimeric antibody receptors (CARs) or engineered T cell receptors. These methods and compositions can be used for the treatment of cancers and the like. Corrected globin genes may be used for patients afflicted with diseases such as sickle cell anemia and corrected common gamma chain genes can be introduced to treat patients with X-linked severe combined immunodeficiency. Wild type genes encoding clotting factors may be used therapeutically for hemophilia patients. For example, wild type or an enhanced Factor VIII gene may be introduced in patients with Hemophilia A, or wild type or enhanced Factor IX genes may be introduced in patients with Hemophilia B.

Additionally, genes involved in lysosomal storage diseases may be used. The most common examples of these diseases and the genes involved are Gaucher's (glucocerebrosidase deficiency-gene name: GBA), Fabry's (α galactosidase deficiency-GLA), Hunter's (iduronate-2-sulfatase deficiency-IDS), Hurler's (alpha-L iduronidase deficiency-IDUA), and Niemann-Pick's (sphingomyelin phosphodiesterase 1 deficiency-SMPD1) diseases. Alternatively, a wild type FoxB3 gene may be introduced in patient stem cells isolated from patients afflicted with IPEX (immune dysregulation polyendocrinopathy enteropathy, X-linked, see van der Vliet and Nieuwenhuis (2007) *Clin Dev Immunol* 2007:89017). In all these non-limiting examples, the donor DNAs can be introduced into the cell genomes through HDR or NHEJ end-capture, depending on donor design. These treatments may be made ex vivo or in vivo, as described above.

The following Examples relate to exemplary embodiments of the present disclosure in which the nuclease comprises a zinc finger nuclease (ZFN) or a TALEN. It will be appreciated that this is for purposes of exemplification only and that other nucleases can be used (e.g. homing endonucleases or meganucleases) with engineered DNA-binding domains and heterologous cleavage domains.

EXAMPLES

Example 1

Design, Construction and General Characterization of Zinc Finger Protein Nucleases (ZFN)

Zinc finger proteins targeted to HPRT were designed and incorporated into plasmids, AAV or adenoviral vectors essentially as described in Urnov et al. (2005) *Nature* 435(7042): 646-651, Perez et al (2008) *Nature Biotechnology* 26(7):808-816, and as described in U.S. Pat. No. 6,534,261. Table 1 shows the recognition helices within the DNA binding domain of exemplary HPRT ZFPs while Table 2 shows the target sites for these ZFPs (DNA target sites indicated in uppercase letters; non-contacted nucleotides indicated in lowercase). Nucleotides in the target site that are contacted by the ZFP recognition helices are indicated in uppercase letters; non-contacted nucleotides indicated in lowercase.

TABLE 1

Mouse and Human HPRT-specific zinc finger nucleases- helix design

| Target species/ SBS # | Design | | | | | |
|---|---|---|---|---|---|---|
| | F1 | F2 | F3 | F4 | F5 | F6 |
| Mouse 29264 | RSDALSR (SEQ ID NO: 1) | DRSALAR (SEQ ID NO: 2) | RSDNLSQ (SEQ ID NO: 3) | ASNDRKK (SEQ ID NO: 4) | RSDNLSA (SEQ ID NO: 5) | RNNDRKT (SEQ ID NO: 6) |
| Mouse 29262 | DRSHLSR (SEQ ID NO: 7) | DRSALAR (SEQ ID NO: 2) | RSDTLSE (SEQ ID NO: 8) | QSSHLAR (SEQ ID NO: 9) | RSDTLSQ (SEQ ID NO: 10) | TRQARIQ (SEQ ID NO: 11) |
| Human 29251 | DRSHLTR (SEQ ID NO: 12) | QSGHLSR (SEQ ID NO: 13) | RSDSLSV (SEQ ID NO: 14) | RSANLTR (SEQ ID NO: 15) | RSDNLSE (SEQ ID NO: 16) | VRRALSS (SEQ ID NO: 17) |
| Human 29250 | RSDNLSE (SEQ ID NO: 16) | TSGSLTR (SEQ ID NO: 18) | DRSNLSR (SEQ ID NO: 19) | QRSNLDS (SEQ ID NO: 20) | RSDNLAR (SEQ ID NO: 21) | DQSYRRT (SEQ ID NO: 22) |
| Human 30179 | DRSHLTR (SEQ ID NO: 12) | QSGHLSR (SEQ ID NO: 13) | RSDSLSV (SEQ ID NO: 14) | RSAALAR (SEQ ID NO: 23) | RSDNLSE (SEQ ID NO: 16) | VRRALSS (SEQ ID NO: 17) |
| Mouse/ human 29223 | RSDSLLR (SEQ ID NO: 24) | QSCARNV (SEQ ID NO: 25) | QSGNLAR (SEQ ID NO: 26) | QSTPRNK (SEQ ID NO: 27) | RSDALSE (SEQ ID NO: 28) | QNATRTK (SEQ ID NO: 29) |
| Mouse/ Human 29216 | DRSALTK (SEQ ID NO: 30) | RSDNLSE (SEQ ID NO: 16) | KRCNLRC (SEQ ID NO: 31) | DRSALSR (SEQ ID NO: 32) | QSGSLTR (SEQ ID NO: 33) | NA |
| Human 11447 | DRSHLSR (SEQ ID NO: 7) | RSDDLTR (SEQ ID NO: 34) | RSDDLTR (SEQ ID NO: 34) | RSDDRKT (SEQ ID NO: 35) | NA | NA |

TABLE 1-continued

Mouse and Human HPRT-specific zinc finger nucleases- helix design

| Target species/ SBS # | Design | | | | | |
|---|---|---|---|---|---|---|
| | F1 | F2 | F3 | F4 | F5 | F6 |
| Human 11443 | RSDDLTR (SEQ ID NO: 34) | RSDALTQ (SEQ ID NO: 36) | TSGSLSR (SEQ ID NO: 37) | DSSDRKK (SEQ ID NO: 38) | NA | NA |
| Human 34270 | QSGHLAR (SEQ ID NO: 79) | QRVALQA (SEQ ID NO: 80) | QSSHLTR (SEQ ID NO: 81) | QSGSLTR (SEQ ID NO: 33) | RDSNLSV (SEQ ID NO: 82) | QKINLQV (SEQ ID NO: 83) |
| Human 34269 | RSDVLSA (SEQ ID NO: 84) | QNATRIN (SEQ ID NO: 85) | QNATRIN (SEQ ID NO: 85) | TSGNLTR (SEQ ID NO: 86) | QSNDLNS (SEQ ID NO: 87) | NA |
| Human 34278 | QSGNLAR (SEQ ID NO: 26) | QSGDLTR (SEQ ID NO: 49) | RSDTLSE (SEQ ID NO: 8) | ARSTRTN (SEQ ID NO: 88) | RSDSLSV (SEQ ID NO: 14) | RSAHLSR (SEQ ID NO: 89) |
| Human 34277 | DRSNLSR (SEQ ID NO: 19) | QKVTLAA (SEQ ID NO: 90) | QSGNLAR (SEQ ID NO: 26) | QGANLIK (SEQ ID NO: 91) | DRSALSR (SEQ ID NO: 32) | QSGDLTR (SEQ ID NO: 49) |
| Human 34306 | TSGSLSR (SEQ ID NO: 37) | QSGNLAR (SEQ ID NO: 26) | QSSDLSR (SEQ ID NO: 92) | RSDHLSQ (SEQ ID NO: 93) | DNSNRIN (SEQ ID NO: 94) | NA |
| Human 34303 | QSGDLTR (SEQ ID NO: 49) | TSGSLTR (SEQ ID NO: 18) | RSDVLSE (SEQ ID NO: 95) | RNQHRKT (SEQ ID NO: 96) | RSAHLSR (SEQ ID NO: 89) | DRSDLSR (SEQ ID NO: 97) |
| Human 34321 | RSDNLSN (SEQ ID NO: 98) | TSSNRKN (SEQ ID NO: 99) | TSGNLTR (SEQ ID NO: 86) | WRSCLRA (SEQ ID NO: 100) | QSGNLAR (SEQ ID NO: 26) | NA |
| Human 35944 | QSSDLSR (SEQ ID NO: 92) | QSGNRTT (SEQ ID NO: 101) | TSSNLSR (SEQ ID NO: 102) | TSGNLTR (SEQ ID NO: 86) | LSQDLNR (SEQ ID NO: 103) | NA |
| Human 35974 | NNRDLIN (SEQ ID NO: 104) | TSSNLST (SEQ ID NO: 105) | HSNARKT (SEQ ID NO: 106) | QSGALAR (SEQ ID NO: 107) | RSDHLSR (SEQ ID NO: 108) | NA |
| Human 35963 | ARSTRTN (SEQ ID NO: 88) | QSGHLAR (SEQ ID NO: 79) | QRVALQA (SEQ ID NO: 80) | ERGTLAR (SEQ ID NO: 109) | RSDALAR (SEQ ID NO: 110) | NA |
| Human 34359 | DRSNLSR (SEQ ID NO: 19) | ARWYLDK (SEQ ID NO: 111) | RSANLTR (SEQ ID NO: 15) | RSDVLSE (SEQ ID NO: 95) | QRSNLKV (SEQ ID NO: 112) | NA |
| Human 35981 | RSDNLAR (SEQ ID NO: 21) | QKVNLRE (SEQ ID NO: 113) | QRTHLTQ (SEQ ID NO: 114) | RSDNLSE (SEQ ID NO: 16) | TRSPLRN (SEQ ID NO: 115) | NA |
| Human 37714 | QSGHLAR (SEQ ID NO: 79) | QSSNRQK (SEQ ID NO: 116) | QSGHLAR (SEQ ID NO: 79) | QSGSLTR (SEQ ID NO: 33) | RSDNLSV (SEQ ID NO: 117) | QNANRIT (SEQ ID NO: 118) |
| Human 37706 | RSDVLSA (SEQ ID NO: 84) | QNATRIN (SEQ ID NO: 85) | QSGDLTR (SEQ ID NO: 49) | TSGNLTR (SEQ ID NO: 86) | QSNDLNS (SEQ ID NO: 87) | NA |
| Human 37741 | LKQHLNE (SEQ ID NO: 119) | QNAHRKT (SEQ ID NO: 120) | DSSHRTR (SEQ ID NO: 121) | RSDHLSQ (SEQ ID NO: 93) | CTRNRWR (SEQ ID NO: 122) | NA |
| Human 37734 | QSGDLTR (SEQ ID NO: 49) | TSGSLTR (SEQ ID NO: 18) | RSDVLSE (SEQ ID NO: 95) | RNQHRKT (SEQ ID NO: 96) | RSDHLSE (SEQ ID NO: 123) | HSRTRTK (SEQ ID NO: 124) |
| Human 37746 | TSGSLSR (SEQ ID NO: 37) | QAGQRRV (SEQ ID NO: 125) | DRSHLAR (SEQ ID NO: 126) | RSDHLSQ (SEQ ID NO: 93) | CTRNRWR (SEQ ID NO: 122) | NA |

TABLE 1-continued

Mouse and Human HPRT-specific zinc finger nucleases- helix design

| Target species/ SBS # | Design | | | | | |
|---|---|---|---|---|---|---|
| | F1 | F2 | F3 | F4 | F5 | F6 |
| Human 37735 | QSGDLTR (SEQ ID NO: 49) | TSGSLTR (SEQ ID NO: 18) | RSDVLSE (SEQ ID NO: 95) | RNQHRKT (SEQ ID NO: 96) | RSDHLSE (SEQ ID NO: 123) | HSRTRTK (SEQ ID NO: 124) |

TABLE 2

Target Sites of Mouse and Human HPRT-specific zinc finger nucleases

| SBS # | Target site |
|---|---|
| 29264 | acCCGCAGTCCCAGcGTCGTGgtgagcc_ (SEQ ID NO: 39) |
| 29262 | gcATGACGGGACCGGTCGGCtcgcggca_ (SEQ ID NO: 40) |
| 29251 | tgATGAAGGAGATGGGAGGCcatcacat (SEQ ID NO: 41) |
| 29250 | atCTCGAGCAAGACGTTCAGtcctacag_ (SEQ ID NO: 42) |
| 30179 | tgATGAAGGAGATGGGAGGCcatcacat_ (SEQID NO: 41) |
| 29223 | aaGCACTGaATAGAAATAGTGatagatc_ (SEQ ID NO: 43) |
| 29216 | atGTAATCCAGCAGGTCagcaaagaatt_ (SEQ ID NO: 44) |
| 11447 | ggCCGGCGcGCGGGCtgactgctcagga_ (SEQ ID NO: 45) |
| 11443 | gcTCCGTTATGGCGacccgcagccctgg_ (SEQ ID NO: 46) |
| 34270 | tgCAAAAGGTAGGAAAAGGAccaaccag (SEQ ID NO: 166) |
| 34269 | acCCAGATACAaACAATGgatagaaaac (SEQ ID NO: 167) |
| 34278 | ctGGGATGaACTCTGgGCAGAAttcaca (SEQ ID NO: 127) |
| 34277 | atGCAGTCTAAGAAtACAGACagatcag (SEQ ID NO: 128) |
| 34306 | tgCACAGGGGCTGAAGTTgtcccacagg (SEQ ID NO: 129) |
| 34303 | tgGCCAGGAGGCTGGTTGCAaacatttt (SEQ ID NO: 130) |
| 34321 | ttGAATGTGATtTGAAAGgtaatttagt (SEQ ID NO: 131) |
| 35944 | aaGCTGATGATtTAAGCTttggcggttt (SEQ ID NO: 132) |
| 35974 | gtGGGGTAATTGATCCAtgtatgccatt (SEQ ID NO: 133) |
| 35963 | ggGTGGCCAAAGGAACTgcgcgaacctc (SEQ ID NO: 134) |
| 34359 | atCAACTGGAGTTGGACtgtaataccag (SEQ ID NO: 135) |
| 35981 | ctTTACAGAGACAAGAGgaataaaggaa (SEQ ID NO: 136) |
| 37714 | tgCAAAAGGTAGGAAAAGGAccaaccag (SEQ ID NO: 166) |
| 37706 | acCCAGATACAaACAATGgatagaaaac (SEQ ID NO: 167) |
| 37741 | tgCACAGGGGCTGAAGTtgtcccacagg (SEQ ID NO: 129) |
| 37734 | tgGCCAGGAGGCTGGTTGCAaacatttt (SEQ ID NO: 130) |
| 37746 | tgCACAGGGGCtGAAGTTgtcccacagg (SEQ ID NO: 129) |
| 37735 | tgGCCAGGAGGCTGGTTGCAaacatttt (SEQ ID NO: 130) |

Example 2

Activity of Murine and Human-Specific HPRT ZFNs

ZFN pairs targeting the murine or the human HPRT gene, as well as a ZFN pair designed to recognize conserved sequences in both the human and murine HPRT gene were used to test the ability of these ZFNs to induce DSBs at a specific target site. In particular, the Cel-I mismatch assay (Surveyor™, Transgenomics; Perez et al, (2008) *Nat. Biotechnol.* 26: 808-816 and Guschin et al, (2010) *Methods Mol Biol.* 649:247-56) was used where PCR-amplification of the target site was followed by quantification of insertions and deletions (indels) using the mismatch detecting enzyme Cel-I (Yang et al, (2000) *Biochemistry* 39, 3533-3541) which provides a lower-limit estimate of DSB frequency. After introduction of the ZFN expression vector at standard conditions (37° C.) into human K562 cells or murine Neuro2A cells as described in Perez, ibid, genomic DNA was isolated from the cells using the DNeasy™ kit (Qiagen). The percent indels indicates the percentage of alleles that were altered by NHEJ following cleavage.

Results from the Cel-I mismatch assay on DNA isolated from K562 cell samples (FIG. 1A) or Neuro 2A cell samples (FIG. 1B) demonstrate that the ZFNs cleave at their respective target sites. Lane identities are as shown, and the percent of PCR products wherein the nucleotides have been inserted or deleted ("indels") are indicated at the bottom of each lane ("% NHEJ").

Example 3

Percent of Modified Cells Following ZFN Treatment and Selection on 6-TG

To test the frequency of targeted modification following selection of the transfected cells on 6-TG, cells were transfected with a combination of HPRT-specific ZFNs (SBS#29251 and SBS#29250, see Table 1 above) and CCR5-specific ZFNs (SBS#8196z and SBS#8266, see co-owned U.S. Pat. No. 7,951,925).

Figure 2:
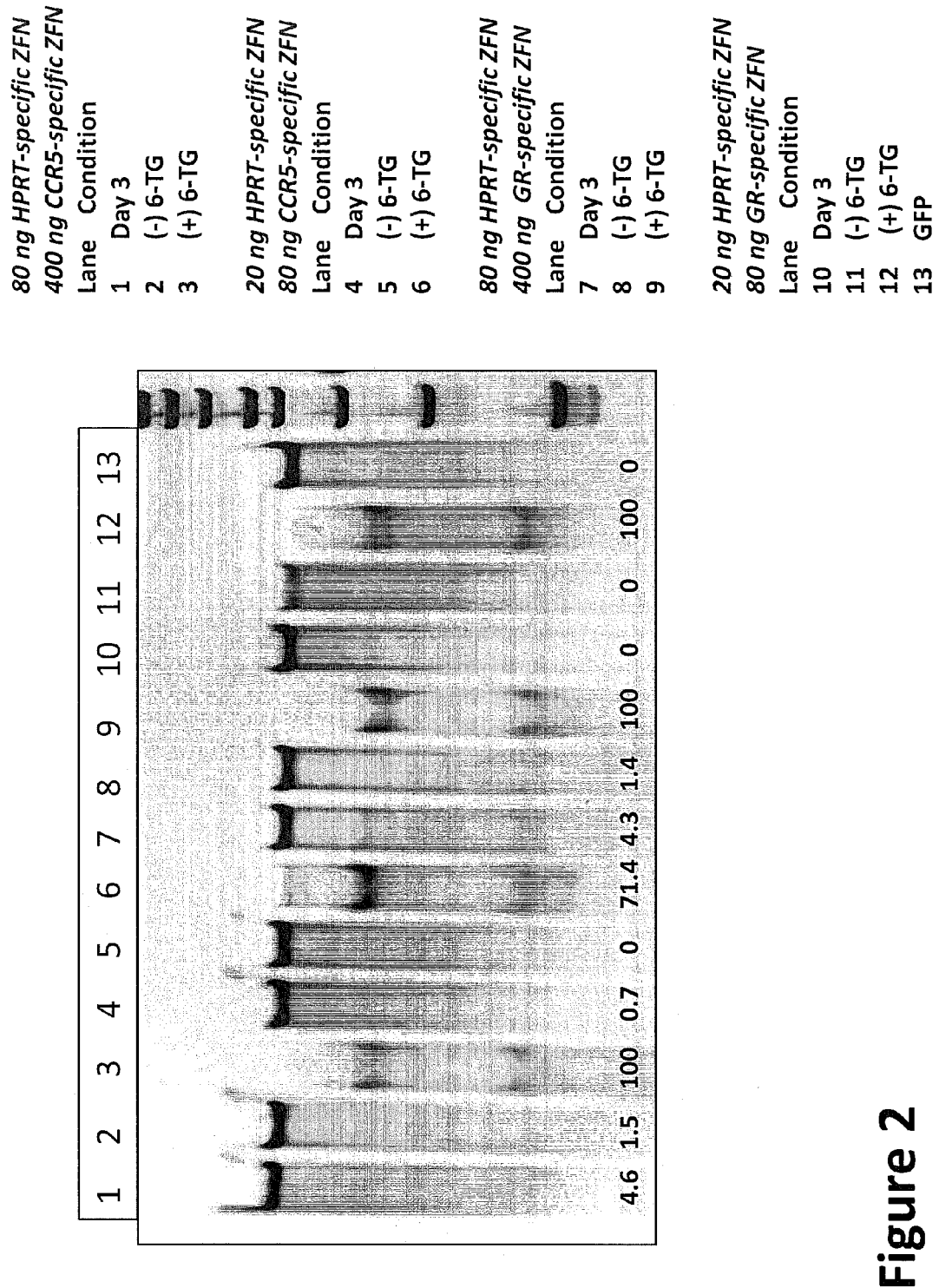
FIG. 2 depicts a gel measuring the percent of indels in cells that were transfected with HPRT specific ZFNs and then treated with 6-TG. The K562 cells were also transfected with ZFN pairs specific for either CCR5 or the glucocorticoid receptor locus (GR). Cel-I experiments (as described above) were performed on cells at the HPRT locus after 10 to 14 days of growth in 6-TG. HPRT resistant cells were only observed in those samples that had been treated with the ZFNs targeting the HPRT locus. The lanes are numbered 1 to 13 at the top and show the following: Lanes 1-3 show Cel-I results using 80 ng HPRT-specific ZFN and 400 ng CCR5-specific ZFNs (see, e.g., U.S. Pat. No. 7,951,925) 3 days after ZFN administration (lane 1) in the absence (lane 2) or presence (lane 3) of 6-TG. Lanes 4-6 show Cel-I results using 20 ng HPRT-specific ZFN and 80 ng CCR5-specific ZFNs (see, e.g., U.S. Pat. No. 7,951, 925) 3 days after ZFN administration (lane 4) in the absence (lane 5) or presence (lane 6) of 6-TG. Lanes 7-9 show Cel-I results using 80 ng HPRT-specific ZFN and 400 ng GR-specific ZFNs (see, e.g., U.S. Patent Publication No. 20080188000) 3 days after ZFN administration (lane 7) in the absence (lane 8) or presence (lane 9) of 6-TG. Lanes 10-13 show Cel-I results using 20 ng HPRT-specific ZFN and 80 ng GR-specific ZFNs (see, e.g., U.S. Patent Publication No. 20080188000) 3 days after ZFN administration (lane 10) in the absence (lane 11) or presence (lane 12) of 6-TG or GFP (lane 13).

Expression plasmids encoding the ZFNs were introduced into K562 cells and three days after transfection, the cells were split into two pools. One pool was selected on a concentration of 6 µM 6-TG and then following selection for 8-11 days, was analyzed by the Cel-I mismatch assay for the presence of indels. The results are shown in FIG. 2. A comparison of the results from cells prior to 6-TG selection, with those selected on 6-TG demonstrated a dramatic enrichment for modified cells. For example, cell pools that initially showed a detectable modification rate of 0-4.6 percent prior to 6-TG selection were measured at 71-100% modification after selection. The PCR products from the 6-TG selected cells were cloned and sequenced, where the sequence analysis demonstrated a modification of all clones sequenced (88 of 88 clones modified).

Example 4

Use of 6-TG Selection for Enrichment of Cleavage at a Second Target Site

The concept that 6-TG selection can also be used to enrich for modification at a second locus by another ZFN pair that was introduced with the HPRT-specific nucleases was then tested. We assumed that such a 'co-selection' would be most efficient if the second ZFN pair was provided in excess of the HPRT ZFN pair and if the activity of the HPRT ZFN pair was weaker than that of the second ZFN pair, which was accomplished by coupling the HPRT ZFN DNA binding domain in the pair to the less active obligate heterodimeric Fok I nuclease domain mutants DD and RR while the DNA binding domains in the second (non-HPRT-targeted) ZFN pair was coupled to the ELD KKR mutant pair. (see co-owned US Patent Publication No. 2011/0201055 and 20110158957). This arrangement has the additional advantage that the DD/RR mutants are orthologous to the more active heterodimeric ELD/KKR FokI mutants, which means that even though four ZFNs are introduced into the cell concurrently, active dimeric ZFN pairs can only be formed from the two desired combinations.

Figure 3:
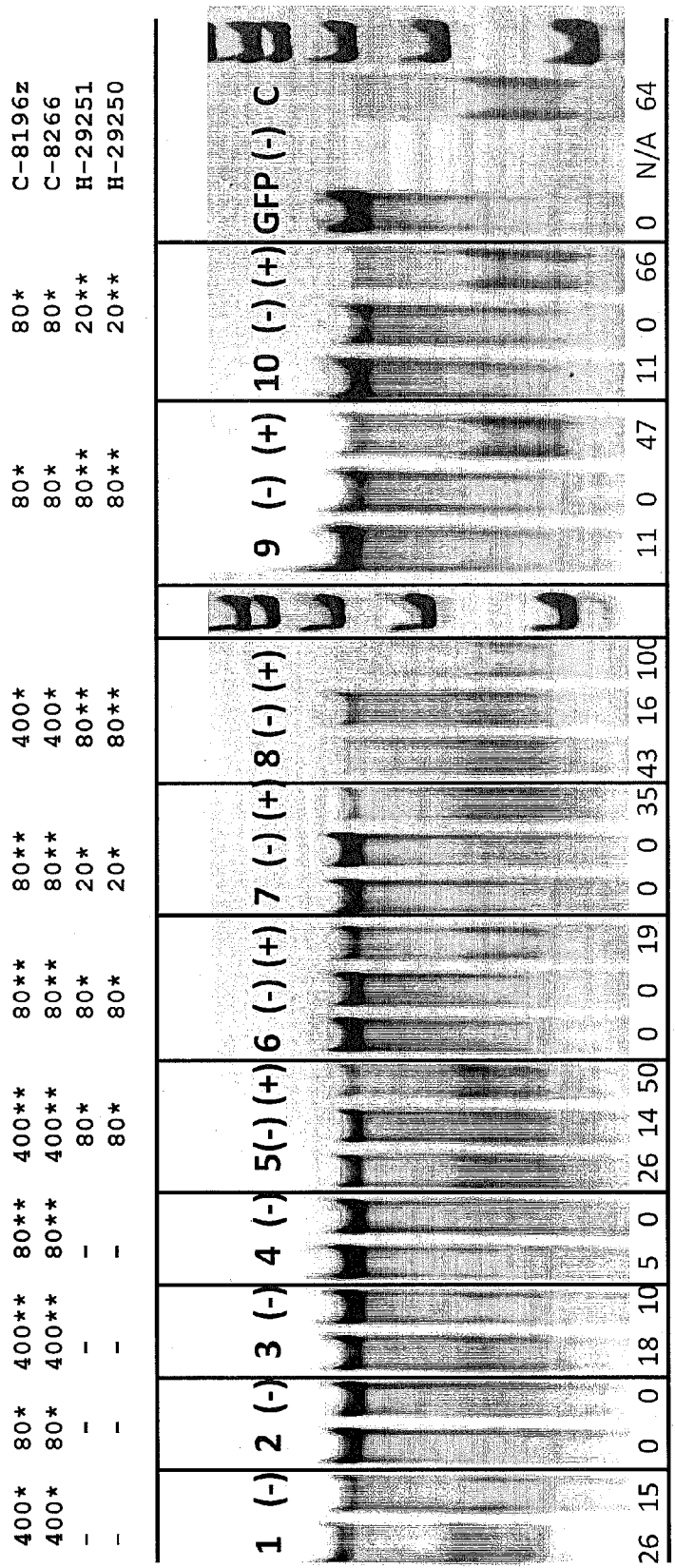
FIG. 3 depicts a gel measuring the percent of indels in K562 cells that were transfected with HPRT specific ZFNs as well as with another pair of ZFNs targeting the CCR5 locus. The cells were then selected on 6-TG. DNA was isolated from the cells following the selection, and the Cel-I assay was performed at the CCR5 locus. As can be seen, selection of the transfected cells on 6-TG enriches cells that had been cleaved at CCR5. Lanes are as follows: Sample number lane (1, 2, etc.) depicts the results of the Cel-I assay performed on DNA harvested three days following transfection. Numbers or (−) above the boxed gel indicate the ngs of DNA used in transfection reaction. "**" indicates the use of a nuclease pair with the engineered, obligate heterodimeric ELD/KKR FokI domains while "*" indicates that the nuclease pair includes the DD/RR FokI obligate heterodimer domains. See, U.S. Patent Publication No. 20110201055. In the sample section, (−) or (+) indicates DNA isolated from cells grown either in the absence or presence of 6-TG, respectively. Percent of modification observed is indicated at the bottom of each lane.

FIG. 3 shows that upon introduction of the 29251/29250 HPRT ZFN pair and a ZFN pair targeting CCR5 into K562 cells, 6-TG selection results in a dramatic enrichment of CCR5 modified cells, demonstrating the utility of the 'co-selection approach' for the enrichment of modification at a second target locus. In this experiment, the CCR5-specific ZFNs used were 8196z and 8266, described above in Example 4, and modification at the CCR5 locus was assayed by the Cel-I mismatch assay. In FIG. 3, above the boxed gel, the ngs of DNA used in the transfections are indicated. The double ("**") or single ("*") asterisks indicate that the FokI obligate heterodimeric pairs ELD/KKR or DD/RR are being used, respectively (see co-owned U.S. Patent Publication Nos. 20080131962 and 20110201055 as well as U.S. Pat. No. 7,914,796). The lane with the experiment number indicates the Cel-I mismatch assay results observed from DNA isolated from cells following recover from transfection, and the (−) indicates the Cel-I mismatch assay results in DNA isolated from cells grown in the absence of 6-TG, while the (+) indicates Cel-I mismatch assay results from DNA isolated from cells grown under the 6-TG selection. The numbers at the bottom of the lanes indicate the percent of NHEJ as measured by the Cel-I mismatch assay.

Example 5

Use of 6-TG Selection for Enrichment of Targeted Donor Insertion

Use of 6-TG selection in K562 cells transfected with the 29251/29250 HPRT ZFN pair and a donor molecule carrying homology to the HPRT locus to enrich of cells that have undergone homologous recombination with introduced the donor at the HPRT locus was also tested. In particular, a donor containing a BamHI restriction site targeted into the HPRT locus was introduced using HPRT ZFNs as described above. In this experiment, three different types of plasmids carrying donor molecules with the restriction site were co-introduced with the nucleases: 8 µg of a donor DNA fragment with short regions (arms) of homology to the targeted HPRT insertion site (359 nucleotides), 8 µg of the same donor but where the donor plasmid contained an enhancer element, and 8 µg of a donor DNA fragment with a long arm of homology (725 nucleotides) to the insertion site. The transfectants were allowed to recover following transfection in the absence of any selection, and then split and grown either in the presence (+) or absence (−) of 6-TG. DNA was isolated at day upon completion of selection (8-11 days) and the region surrounding the insertion site was amplified by PCR. The PCR products were then subjected to restriction digestion with the BamHI enzyme.

Figure 4:
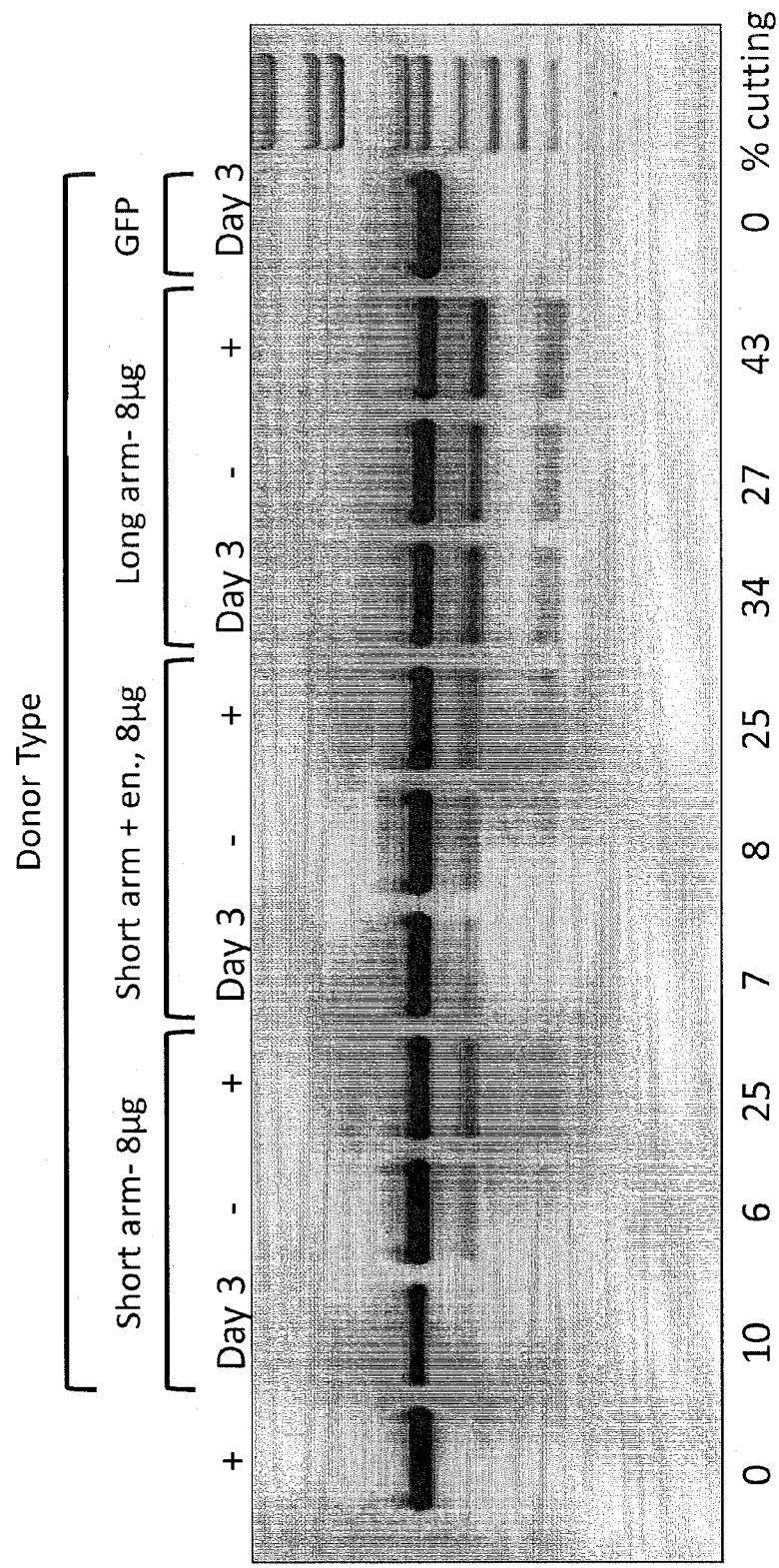
FIG. 4 depicts a gel measuring the percent cutting at a restriction site introduced into the HPRT locus. The K562 cells were transfected with vectors comprising the HPRT-specific ZFNs. Donor molecules were also included comprising the novel restriction site and either a shorter (359 nucleotides) or a longer (725 nucleotides) region of homology with the HPRT locus flanking the insertion site ("arms"). All donors were introduced using a plasmid based approach, but in one set of experiments, the donor plasmid additionally carried an enhancer element ("short arm+en"). All conditions were successful in introducing the donor carrying the restriction site into the HPRT locus which was enriched up to 3-fold and up to levels exceeding 40% of the alleles when 6-TG selection was used.

As shown in FIG. 4, donor integration was enriched up to 3-fold and up to levels exceeding 40% of the alleles when 6-TG selection was used. Numbers at the bottom of the lanes indicate the percent of the PCR product that was cut by the enzyme ("% cutting"). Up to 43% of the DNA contained the donor DNA at the HPRT locus as measured by cutting with the restriction enzyme when the transfectants were selected on 6-TG.

Next, integration of a GFP transgene into the HPRT locus was accomplished in K562 cells using a similar experimental scheme. In this experiment, two donor concentrations were used, where the donor either had short (359 nucleotides) or long (725 nucleotides) regions of homology flanking the HPRT insertion site.

The percent integration of the transgene was determined using the semi-quantitative PCR assay as follows. Three primers (FIG. 5B) that either amplified a product that was specific for the targeted integration of the transgene (primers 15512f+pgkr1) or a product that was specific for the wild type HPRT locus lacking the insertion (primers 15512f+r1-16078) were used and the ratio of the two PCR products determined. The sequences of the primers used were:

```
15512f:
                                        (SEQ ID NO: 58)
5' AGCCACTGGCCCAGTTTCTACAGTCTC 3' pgkr1:
                                        (SEQ ID NO: 59)
5' GACGTGCGGCTTCCGTTTGTC 3' r1-16078:
                                        (SEQ ID NO: 60)
5' GCCTCCCATCTCCTTCATCACAT 3'
```

Figure 5:
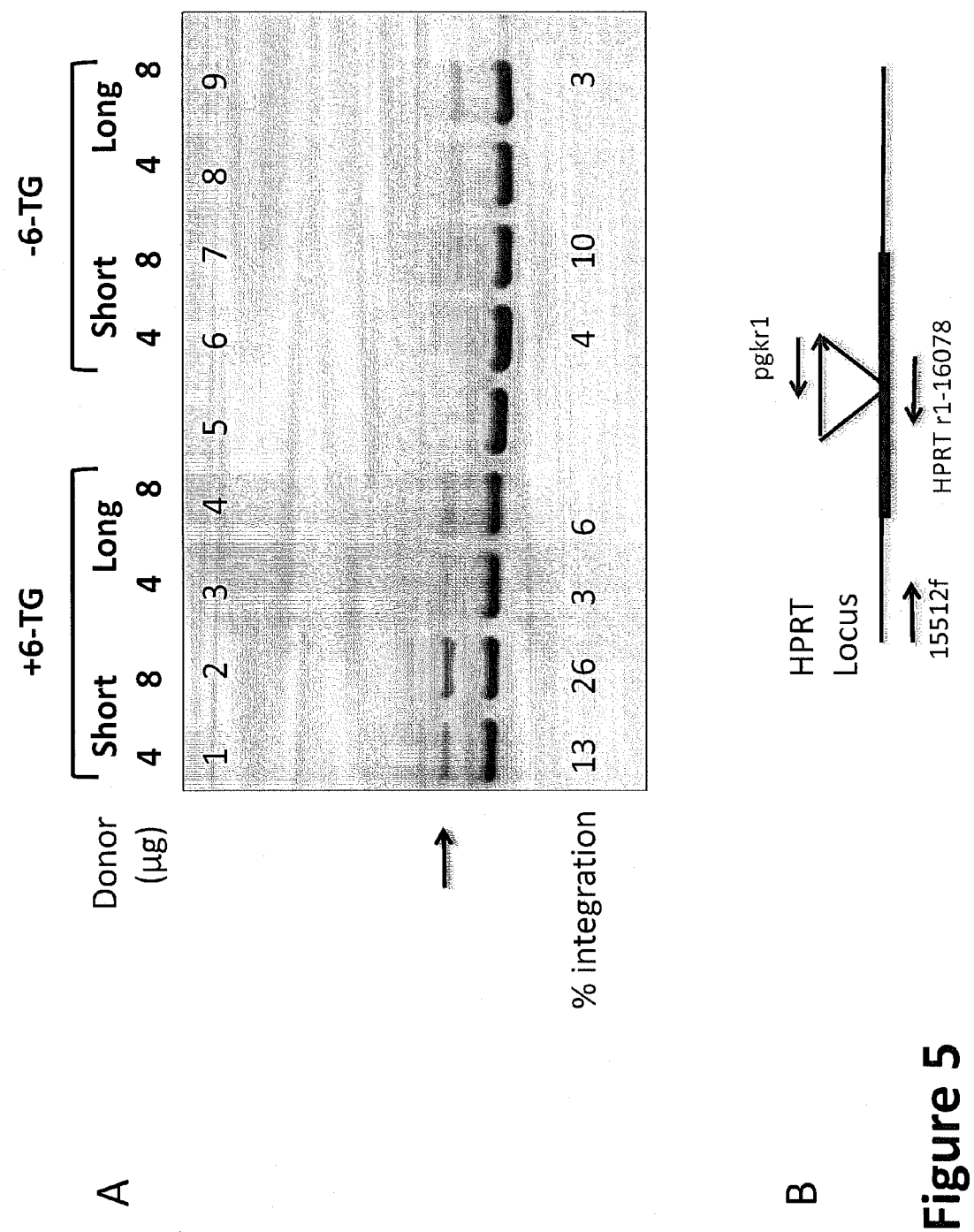
FIG. 5, panels A and B, depict the integration of a GFP transgene into the HPRT locus in K562 cells.

As shown in FIG. 5, and as with the insertion of the restriction site described above, integration of the GFP transgene donor was also enriched 2-3 fold by 6-TG selection as measured in the semi-quantitative PCR based assay. The PCR product indicative of transgene integration is shown by the arrow in FIG. 5A. Up to 26% insertion of the transgene into the HPRT locus was detected, with a 2-3 fold enrichment on targeted integration upon 6-TG selection.

Example 5

Use of 6-TG Selection for Gene Correction of Human Beta Globin

We then tested modification of the human beta-globin locus by a targeted integration donor after co-transfection with beta-globin targeted ZFNs, HPRT ZFNs and selection using 6-TG. In this experiment, cells were transfected with HPRT ZFNs and with the beta globin-specific ZFNs shown in Table 3 below:

TABLE 3

Human beta globin specific zinc finger nucleases

| SBS #, Target | Design | | | | |
|---|---|---|---|---|---|
| | F1 | F2 | F3 | F4 | F5 |
| SBS # 26755 ggGCAGTAA CGGCAGACt tctcctca gg (SEQ ID NO: 47) | DRSNLSR (SEQ ID NO: 19) | QSGDLTR (SEQ ID NO: 49) | RSDTLSQ (SEQ ID NO: 10) | QSGSLTR (SEQ ID NO: 33) | QNATRIK (SEQ ID NO: 50) |
| SBS # 26758 tgGGGcAAG GTGAACGTG gatgaagtt g (SEQ ID NO: 48) | RSDSLSR (SEQ ID NO: 51) | DSSNRKT (SEQ ID NO: 52) | RSAALSR (SEQ ID NO: 53) | RLDNRTA (SEQ ID NO: 54) | RSSHLSR (SEQ ID NO: 55) |

The donor comprised ~1.1 kb of homology of the beta-globin gene flanking the sickle mutation into which a HhaI restriction site was introduced. Two concentrations of the 29251/29250 HPRT-specific ZFNs were used, low (20 ng of each ZFN per reaction) and high (80 ng of each ZFN). Following recovery from transfection, the cells were split and half were subject to 6-TG selection. At completion of selection, DNA was isolated and the targeted region around the beta globin was PCR amplified. For this experiment, the following primers were used:

```
Betaglobin F:
                               (SEQ ID NO: 56)
CCAGAAGGTTTTAATCCAAATAAGGAGAAGATATG Betaglobin R:
                               (SEQ ID NO: 57)
AACGATCCTGAGACTTCCACACTGATGC
```

Figure 6:
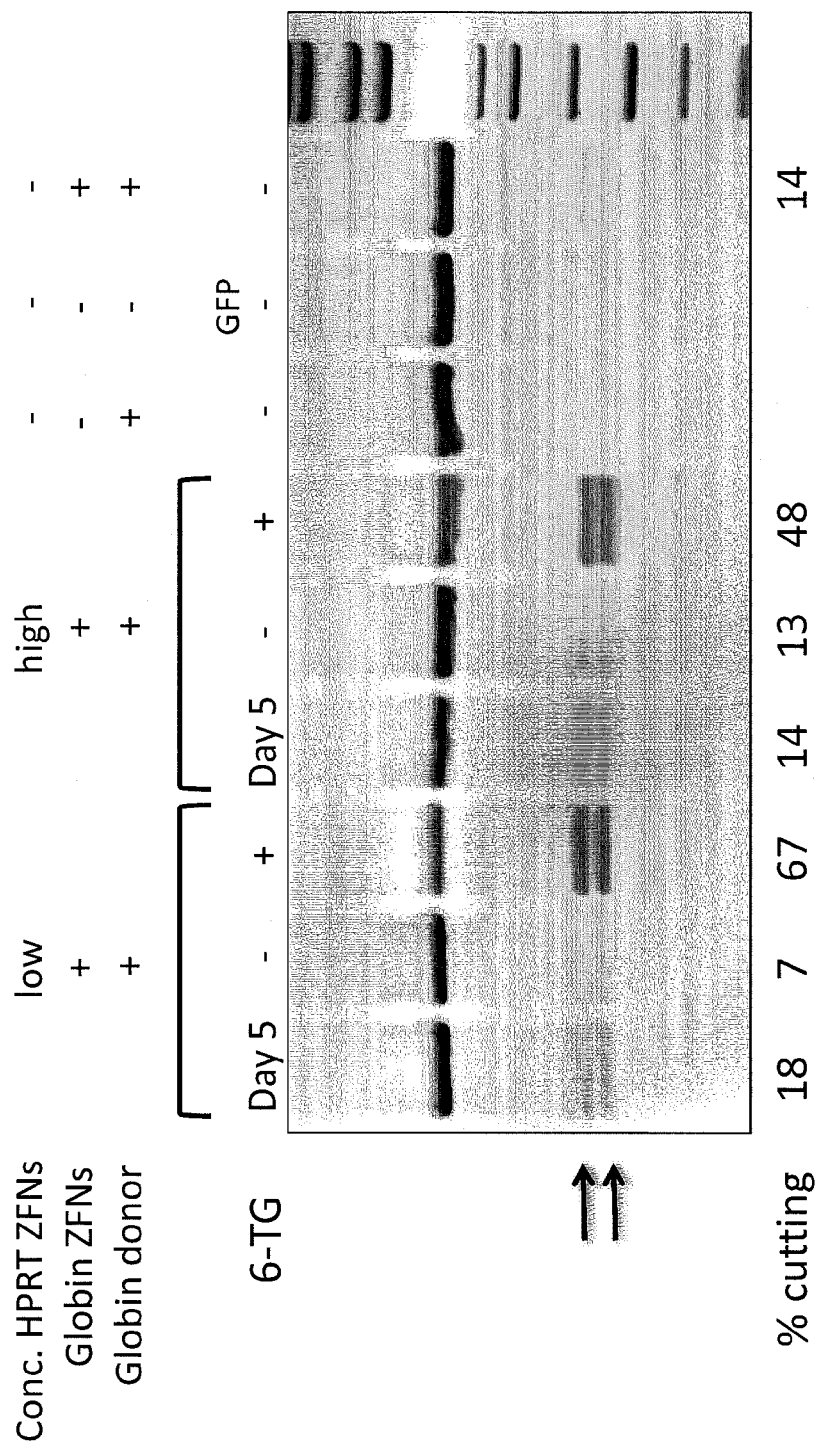
FIG. 6 is a gel depicting the results of a restriction enzyme digestion following targeted integration of a donor containing a HhaI restriction site into the β-globin locus. In this experiment, the donor was inserted into the β-globin locus in K562 cells following co-transfection of ZFNs specific for HPRT, ZFNs specific for beta-globin and the beta-globin specific donor. After recovery from transfection, the cells were split and one group was selected with 6-TG. DNA was isolated from the cells and the β-globin locus was PCR amplified, and then subject to restriction digestion with HhaI A dramatic increase in the frequency of Hha I specific fragments related to successful gene insertion (indicated by arrows) at the beta globin locus was observed following the 6-TG selection.

The PCR product contains the HhaI restriction site, and following amplification of the targeted beta globin locus, cleavage of the PCR product with the HhaI restriction enzyme produces two fragments if the donor integration has occurred. As shown in FIG. 6, a dramatic increase in gene correction frequency at the beta globin locus in the 6-TG selected cells was observed, indicating cleavage with HhaI occurred and demonstrating that selection on 6-TG can result in a cell pool that contained 67% gene correction.

Example 6

Modification of HPRT in Human CD34 Cells

HPRT ZFN expression plasmids were transfected into peripheral blood mobilized hematopoietic stem cells (CD34+ cells from a male donor, i.e. these cells only had one copy of the HPRT gene per cell). Briefly, 200,000 cells were transfected by Amaxa nucleofection as described in Perez, ibid. In this experiment, two sets of HPRT specific ZFNs were used, either the 29251/29250 pair or the 30179/29250 pair at two concentrations, either 200 (+) or 400 (++) ng of each ZFN expression plasmid per nucleofection. Following recovery from the transfection, cells were split into pools and grown in the presence or absence of 6-TG. After selection was complete, modification at the HPRT locus was analyzed by the Cel-I mismatch assay as described in Example 3.

Figure 7:
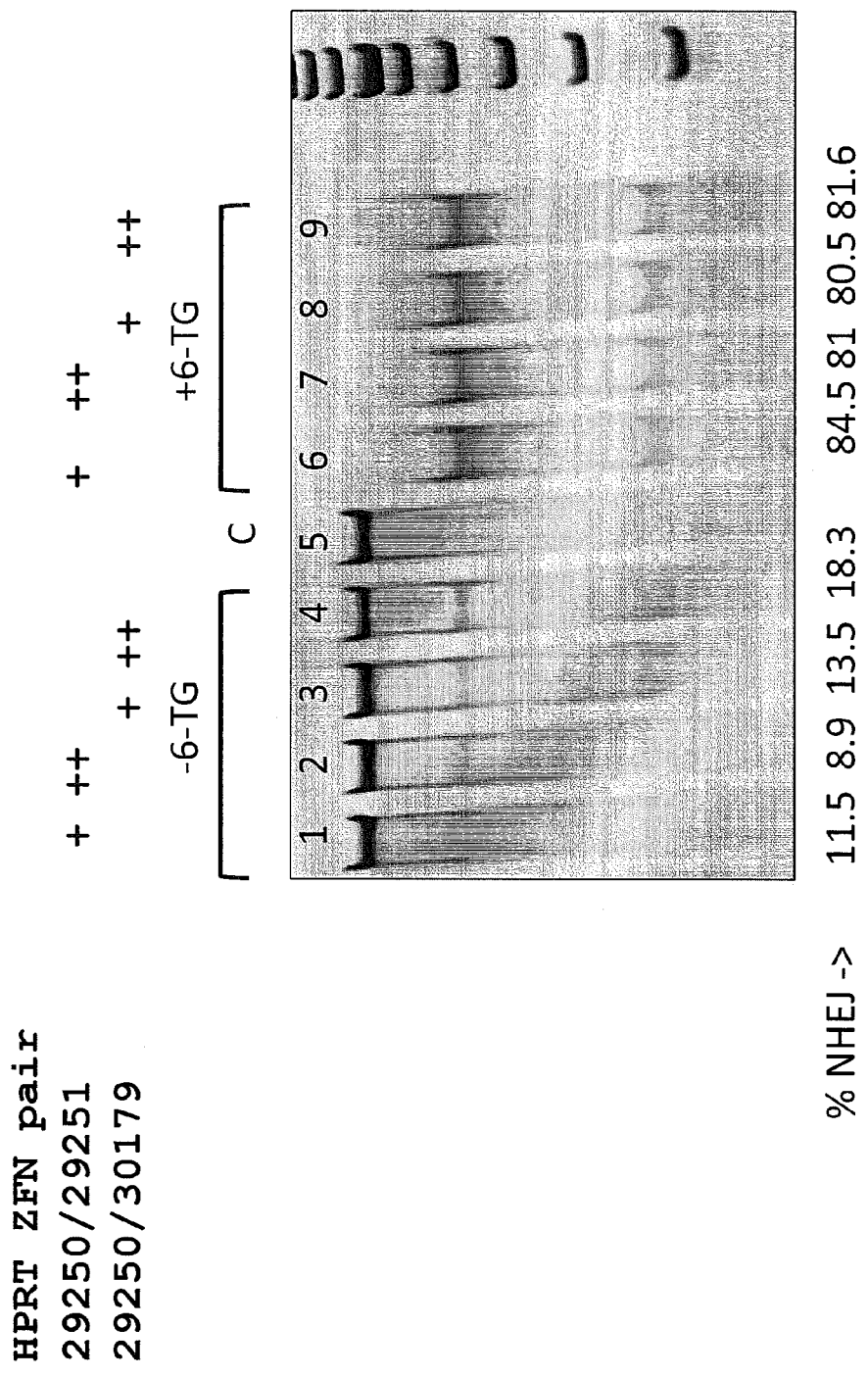
FIG. 7 is a gel depicting modification of the HPRT locus in mobilized human CD34+ stem cells. HPRT specific ZFN expression plasmids were transfected into CD34+ cells and after recovery from the nucleofection, they were split and selected on 6-TG. Modification of the HPRT locus was analyzed by the Cel-I assay as described above and the percent of indels is shown at the bottom of each lane. 6-TG selection increased the percentage of HPRT modified genomes in the cell pool.

As shown in FIG. 7, in the presence of the 6-TG selection, up to 84% of the amplified DNA showed modification at the HPRT locus. The frequency of modification of the HPRT locus in the various samples is listed below each lane. "C" indicates a control nucleofection with a GFP encoding plasmid.

Example 7

Modification of HPRT Using TALENs

TALENs specific for HPRT were also tested in K562 cells. For these experiments, ten different TALENs were constructed wherein the FokI domain was attached to a +63 C-terminal TALE variant (see U.S. patent application Ser. No. 13/068,735). The target nucleotide and RVDs used for each position are shown below in Table 4. In the table, the target nucleotides for the R0 and half repeats are shown at each side of the target sequence and the identities of each RVD in each repeat unit (second row in each set) are shown below the identity of each target nucleotide (first row in each set) (SEQ ID NOs:69-78). The TALENs constructed range from 11-16 full repeats, thus in Table 4, the TALENs that have less than 16 repeats have (N/A) in positions 15, 14, 13, or 12 as is necessary.

TABLE 4

Target and RVDs for HPRT-specific TALENs
(Table 4 discloses SEQ ID NOS 69-78, respectively, in order of appearance)

5'---target sequence---3'

| SBS# | | R0 | 1 | 2 | 3 | 4 | 5 | 6 | 7 | 8 | 9 | 10 | 11 | 12 | 13 | 14 | 15 | 16 | Half Repeat | |
|---|---|---|---|---|---|---|---|---|---|---|---|---|---|---|---|---|---|---|---|---|
| 101288 | 5' | t | G | G | A | T | C | T | A | T | C | A | C | T | A | T | T | (N/A) | T | 3' |
| | | | NN | NN | NI | NG | HD | NG | NI | NG | HD | NI | HD | NG | NI | NG | NG | (N/A) | NG | |
| 101270 | 5' | t | G | C | T | C | A | C | C | A | C | G | A | (N/A) | (N/A) | (N/A) | (N/A) | (N/A) | C | 3' |
| | | | NN | HD | NG | HD | NI | HD | RD | NI | HD | NN | NI | (N/A) | (N/A) | (N/A) | (N/A) | (N/A) | HD | |
| 101267 | 5' | t | C | C | G | T | T | A | T | G | G | C | G | A | (N/A) | (N/A) | (N/A) | (N/A) | C | 3' |
| | | | HD | HD | NN | NG | NG | NI | NG | NN | NN | HD | NN | NI | (N/A) | (N/A) | (N/A) | (N/A) | HD | |
| 101272 | 5' | t | G | G | G | C | C | T | G | A | A | C | C | G | G | C | (N/A) | (N/A) | C | 3' |
| | | | NN | NN | NN | HD | HD | NG | NN | NI | NI | HD | HD | NN | NN | HD | (N/A) | (N/A) | HD | |
| 101271 | 5' | t | G | G | C | G | T | C | G | T | G | G | T | G | A | G | (N/A) | (N/A) | C | 3' |
| | | | NN | NN | HD | NN | NG | HD | NN | NG | NN | NN | NG | NN | NI | NN | (N/A) | (N/A) | HD | |

TABLE 4-continued

Target and RVDs for HPRT-specific TALENs
(Table 4 discloses SEQ ID NOS 69-78, respectively,
in order of appearance)
5'---target sequence---3'

| SBS# | R0 | 1 | 2 | 3 | 4 | 5 | 6 | 7 | 8 | 9 | 10 | 11 | 12 | 13 | 14 | 15 | 16 | Half Repeat |
|---|---|---|---|---|---|---|---|---|---|---|---|---|---|---|---|---|---|---|
| 101286 5' | t | C | T | A | T | C | A | C | T | A | T | T | T | C | T | A | (N/A) | T 3' |
| | | HD | NG | NI | NG | HD | NI | HD | NG | NI | NG | NG | NG | HD | NG | NI | (N/A) | NG |
| 101284 5' | t | T | G | C | T | G | A | C | C | T | G | C | T | G | G | A | T | T 3' |
| | | NG | NN | HD | NG | NN | NI | RD | HD | NG | NN | HD | NG | NN | NN | NI | NG | NG |
| 101282 5' | t | T | T | G | C | T | G | A | C | C | T | G | C | T | G | G | A | T 3' |
| | | NG | NG | NN | HD | NG | NN | NI | HD | HD | NG | NN | HD | NG | NN | NN | NI | NG |
| 101276 5' | t | G | T | A | G | G | A | C | T | G | A | A | C | G | T | C | T | T 3' |
| | | NN | NG | NI | NN | NN | NI | HD | NG | NN | NI | NI | RD | NN | NG | HD | NG | NG |
| 10 5' | t | G | G | C | C | T | C | C | C | A | T | C | T | C | C | (N/A) | (N/A) | T 3' |
| | | NN | NN | HD | HD | NG | HD | HD | HD | NI | NG | HD | NG | HD | HD | (N/A) | (N/A) | NG |

The TALEN pairs were introduced into K562 cells and 3 or 11 days following introduction, DNA was isolated from the cells, the region surrounding the HPRT locus PCR amplified, and then subjected to the Cel-I mismatch assay as above.

Figure 8:
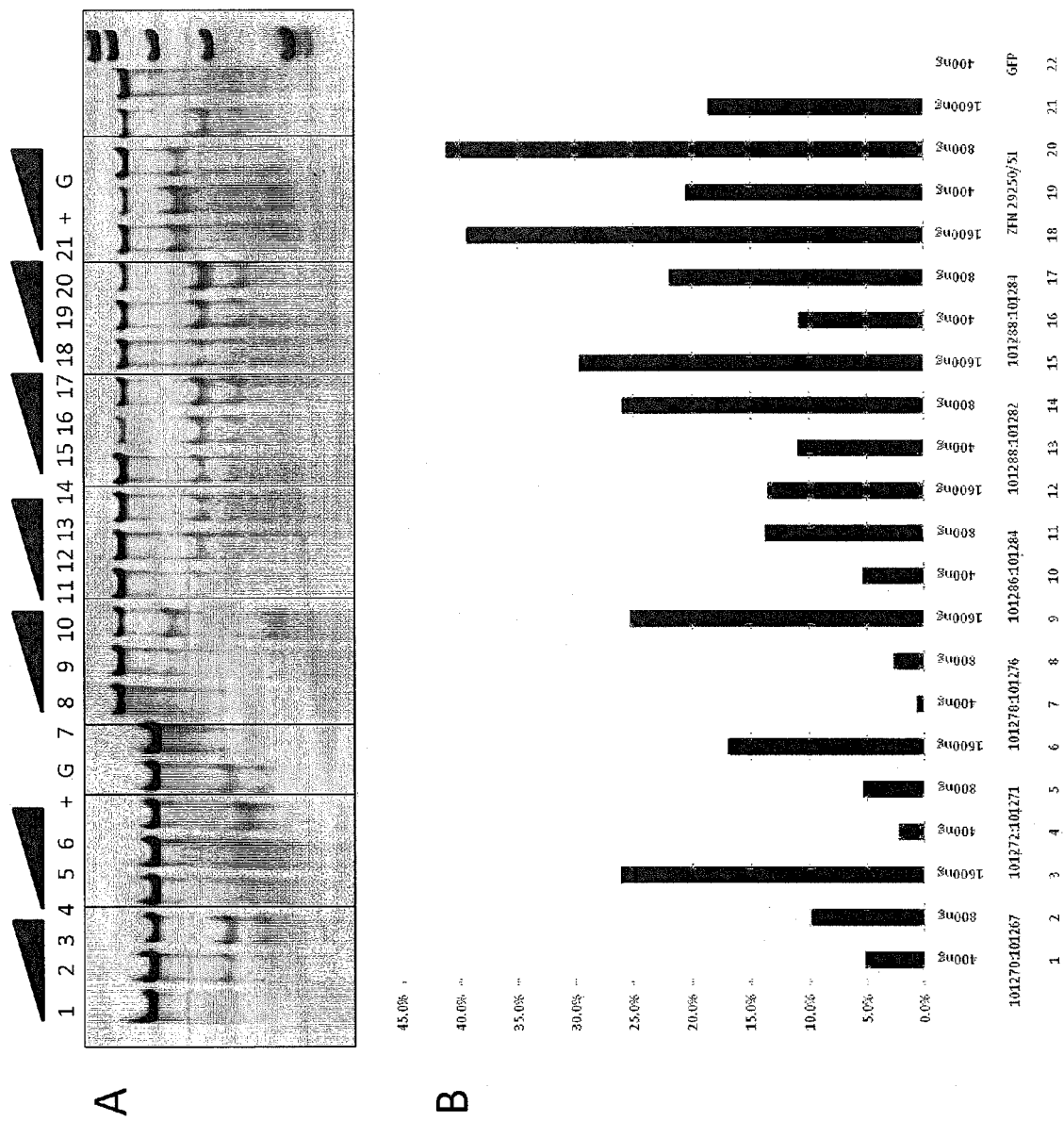
FIG. 8, panels A and B, depict modification of the HPRT locus in K562 cells using HPRT-specific TALENs.

As shown in FIG. 8 and Table 5, TALENs modified the HPRT locus. FIG. 8A depicts the gel from the Cel-I mismatch assay on the day 11 samples, and FIG. 8B shows the percent of modification at the HPRT locus at day 11. Triangles over the lanes in FIG. 8A indicate the increasing concentration of TALEN expression vector in each grouping (see, Table 5 below). The lanes identities are shown below in Table 5 where 'DNA conc.' indicates the amount of expression plasmid that was used in each condition and both the modification or "% NHEJ" results for both day 3 and day 11 are given.

TABLE 5

Lane contents and experimental details

| Lane | ZFN/TALEN Pair | DNA conc. | day 11 % NHEJ | day 3 % NHEJ |
|---|---|---|---|---|
| 1 | 101270:101267 | 400 ng | 5.2% | 4.5% |
| 2 | | 800 ng | 9.9% | 12.5% |
| 3 | | 1600 ng | 26.2% | 31.8% |
| 4 | 101272:101271 | 400 ng | 2.3% | 3.4% |
| 5 | | 800 ng | 5.4% | 7.6% |
| 6 | | 1600 ng | 17.0% | 19.1% |
| + | 101270:101267 | 800 ng | 15.3% | N/A |
| G | GFP | 400 ng | 0.0% | 0.0% |
| 7 | 101278:101276 | 400 ng | 0.7% | 1.7 |
| 8 | | 800 ng | 2.7% | 10.1 |
| 9 | | 1600 ng | 25.4% | 35.3 |
| 10 | 101286:101284 | 400 ng | 5.4% | 25.6 |
| 11 | | 800 ng | 13.8% | 28.4 |
| 12 | | 1600 ng | 13.6% | 35.3 |
| 13 | 101288:101282 | 400 ng | 11.1% | 17.7 |
| 14 | | 800 ng | 26.1% | 33.4 |
| 15 | | 1600 ng | 29.7% | 46.2 |
| 16 | 101288:101284 | 400 ng | 10.9% | 24.8 |
| 17 | | 800 ng | 22.0% | 34.6 |
| 18 | | 1600 ng | 39.5% | 62.2 |
| 19 | ZFN 29250/51 | 400 ng | 20.6% | 30.4 |
| 20 | | 800 ng | 41.3% | 69.2 |
| 21 | | 1600 ng | 18.6% | 38.8 |
| + | 101288:101282 | 800 ng | 26.9% | |
| G | GFP | 400 ng | 0.0% | 0.0 |

Thus, HPRT-specific TALENs are capable of efficiently cleaving the HPRT locus.

Example 8

Cleavage of Canine HPRT

Figure 9:
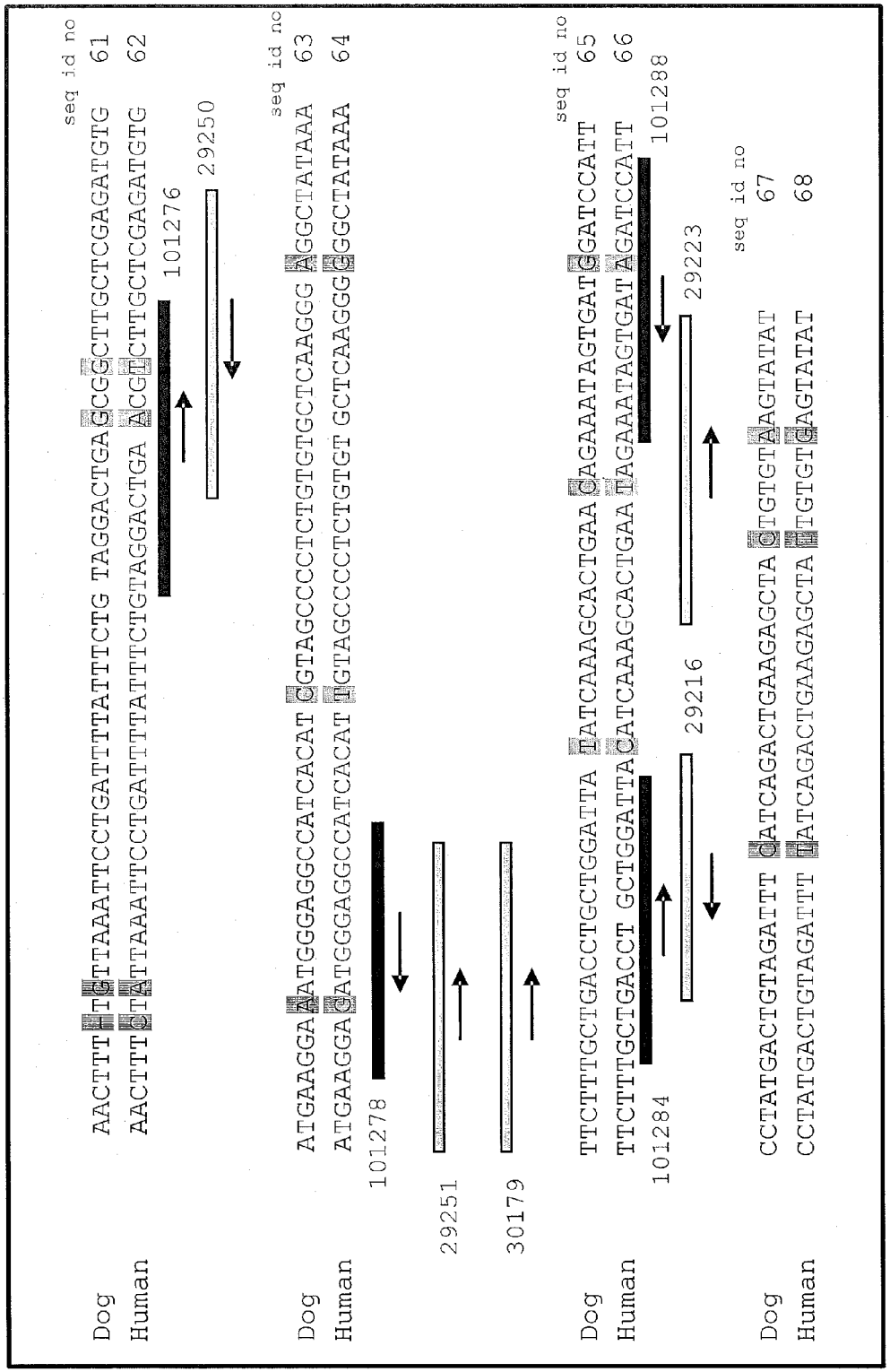
FIG. 9 is an alignment of the DNA sequences in the canine and human HPRT locus corresponding to the target region cleaved by the ZFN and TALEN nucleases. The canine ("dog") DNA sequence is shown on the top of each pair of sequences (SEQ ID NOs:61, 63, 65 and 67, as indicated in the Figure) and the human DNA sequence is shown below (SEQ ID NOs:62, 64, 66 and 68, as indicated in the Figure). Text in the sequences that is in grey highlight indicates nucleotides that are not homologous between the two DNA sequences. Black boxes under the aligned DNA sequences indicate the TALEN binding sites while grey outlined boxes indicate the ZFN binding sites. Arrows indicate which DNA strand the nucleases bind to with the left-to-right arrows indicating a binding site on the 5'-3' or Watson strand and a right-to-left arrow indicating a binding site on the 3'-to-5' or Crick strand.

The HPRT1 specific nuclease pairs were then tested in canine cells in vitro. In these experiments, the lead human HPRT1 ZFN and TALEN nuclease pairs were used, and the alignment of the human and canine (dog) sequences surrounding the nuclease targets sites is shown in FIG. 9. Inspection of the alignment of the human and canine sequences reveals similarity at the target sites. Thus, the nuclease pairs were transfected into the dog cell line D17 by nucleofection of various amounts of the corresponding nuclease expression vectors. The pairs tested and quantities of DNA used in the nucleofection are shown below in Table 6 where the lanes correspond to FIG. 10:

TABLE 6

Cleavage of canine HPRT

| Lane | nuclease pair | Conc. of DNA (ng) | % NHEJ |
|---|---|---|---|
| 1 | 29251:29250 | 100 | 0.0 |
| 2 | 30179:29250 | 100 | 9.2 |
| 3 | 29223:29216 | 100 | 0.0 |
| 4 | 101284:101288 | 100 | 25.1 |
| 5 | 101276:101278 | 100 | 0.0 |
| 6 | GFP (control) | 100 | 0.0 |
| 7 | 29251:29250 | 200 | 2.8 |
| 8 | 30179:29250 | 200 | 4.7 |
| 9 | 29223:29216 | 200 | 0.0 |
| 10 | 101284:101288 | 200 | 16.2 |
| 11 | 101276:101278 | 200 | 2.5 |
| 12 | GFP (control) | 200 | 0.0 |
| 13 | 29251:29250 | 400 | 0.0 |
| 14 | 30179:29250 | 400 | 0.0 |
| 15 | 29223:29216 | 400 | 0.0 |
| 16 | 101284:101288 | 400 | 14.3 |
| 17 | 101276:101278 | 400 | 0.0 |
| 18 | GFP (control) | 400 | 0.0 |
| 19 | Mock (control) | — | 0.0 |

Figure 10:
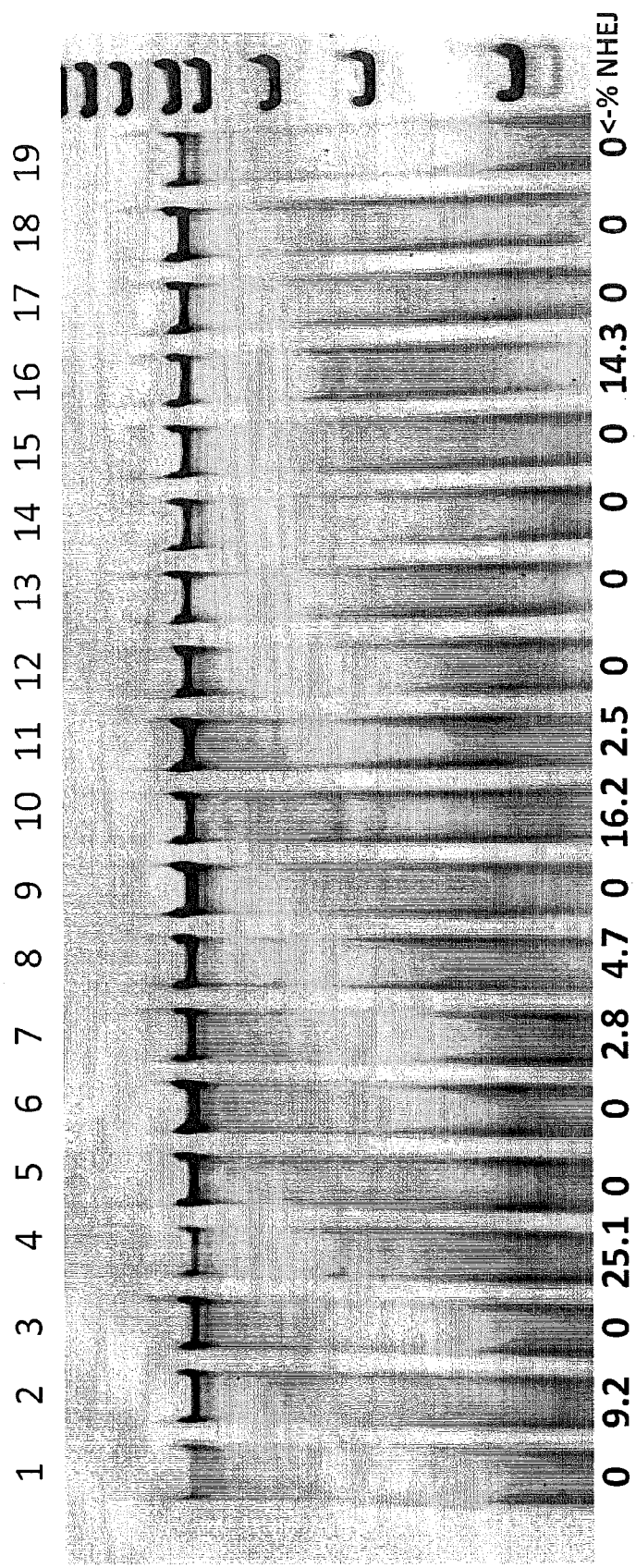
FIG. 10 depicts a gel showing the results of a Cel-I mismatch assay on DNA isolated from the canine cell line D17 that had been transfected with various human HPRT-specific nuclease pairs (individual lanes are identified in Table 6 below). The percent of modification detected ("% NHEJ") is shown at the bottom of each lane.

Analysis of gene modification levels with a PCR primer pair specific for the dog HPRT locus followed by Cel-I mismatch assay showed that some nuclease pairs modified the dog HPRT locus very efficiently (see FIG. 10 and Table 6). The efficiency of gene modification of the various nuclease pairs correlates well with the degree of conservation of the respective binding sites between the human and dog HPRT genes.

Example 9

Cleavage of Rhesus HPRT

The binding sites of the lead human specific ZFN and TALEN HPRT pairs are conserved between human and the rhesus monkey. Therefore, we tested these nucleases against the rhesus cell line LLC-MK2, and found as expected, that the nucleases demonstrated efficient cleavage.

Figure 11:
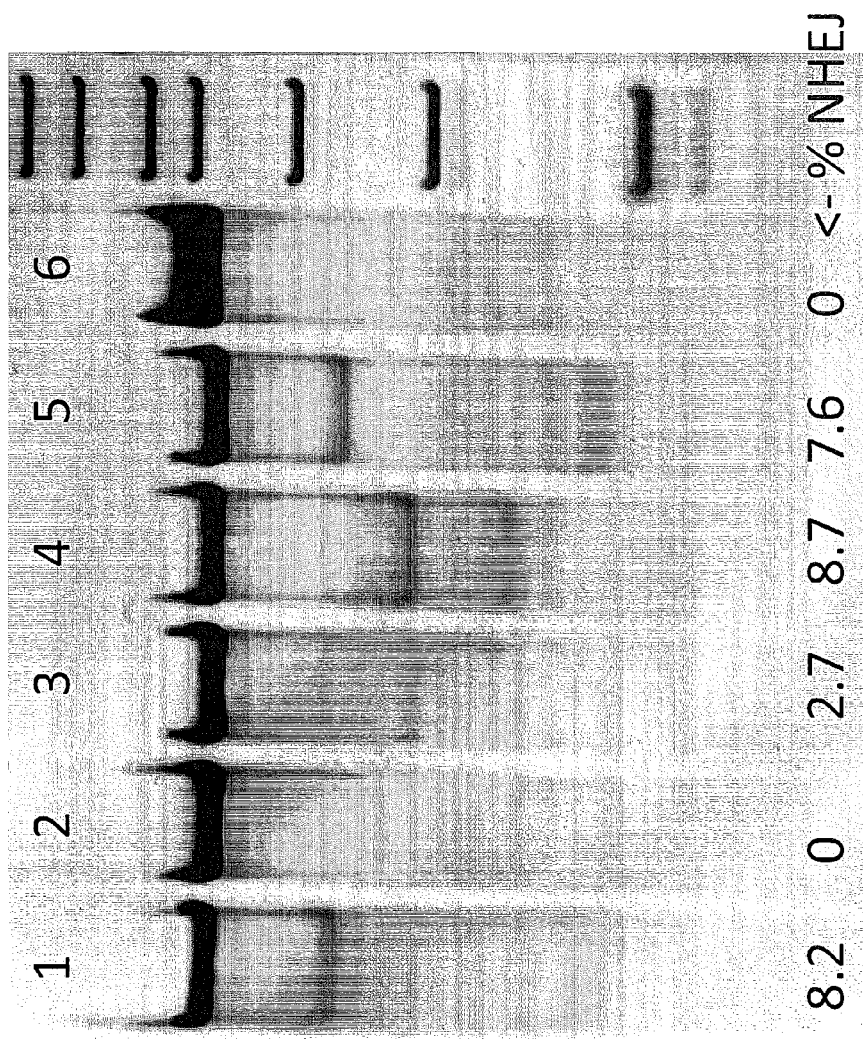
FIG. 11 depicts a gel showing the results of a Cel-I mismatch assay on DNA isolated from the rhesus monkey cell line LLC-MK2 that had been transfected with various human HPRT-specific nuclease pairs. The percent of modification detected ("% NHEJ") is shown at the bottom of each lane.

The nuclease pairs used and percent modification observed of HPRT as determined by the Cel-I mismatch assay, are shown below in Table 7 and the gel analysis is shown in FIG. 11.

TABLE 7

Modification of rhesus monkey HPRT

| Lane | nuclease pair | % NHEJ |
|---|---|---|
| 1 | 29251:29250 | 8.2 |
| 2 | 30179:29250 | 0.0 |
| 3 | 29233:29216 | 2.7 |
| 4 | 101284:101288 | 8.7 |
| 5 | 101276:101278 | 7.6 |
| 6 | GFP | 0.0 |

These data demonstrate that the human-specific nucleases that modify the HPRT locus are also capable of modifying the rhesus monkey HPRT gene.

Example 10

Cleavage of Human HPRT Introns

ZFN pairs shown below in Table 8 were transfected as mRNA into either CD34+ cells (pairs A-F) or into K562 cells (pair A') via BTX® transfection according to manufacturer's protocol. For each transfection, 250,000 cells were used. DNA was harvested by standard procedures on day 3 post-transfection.

Figure 12:
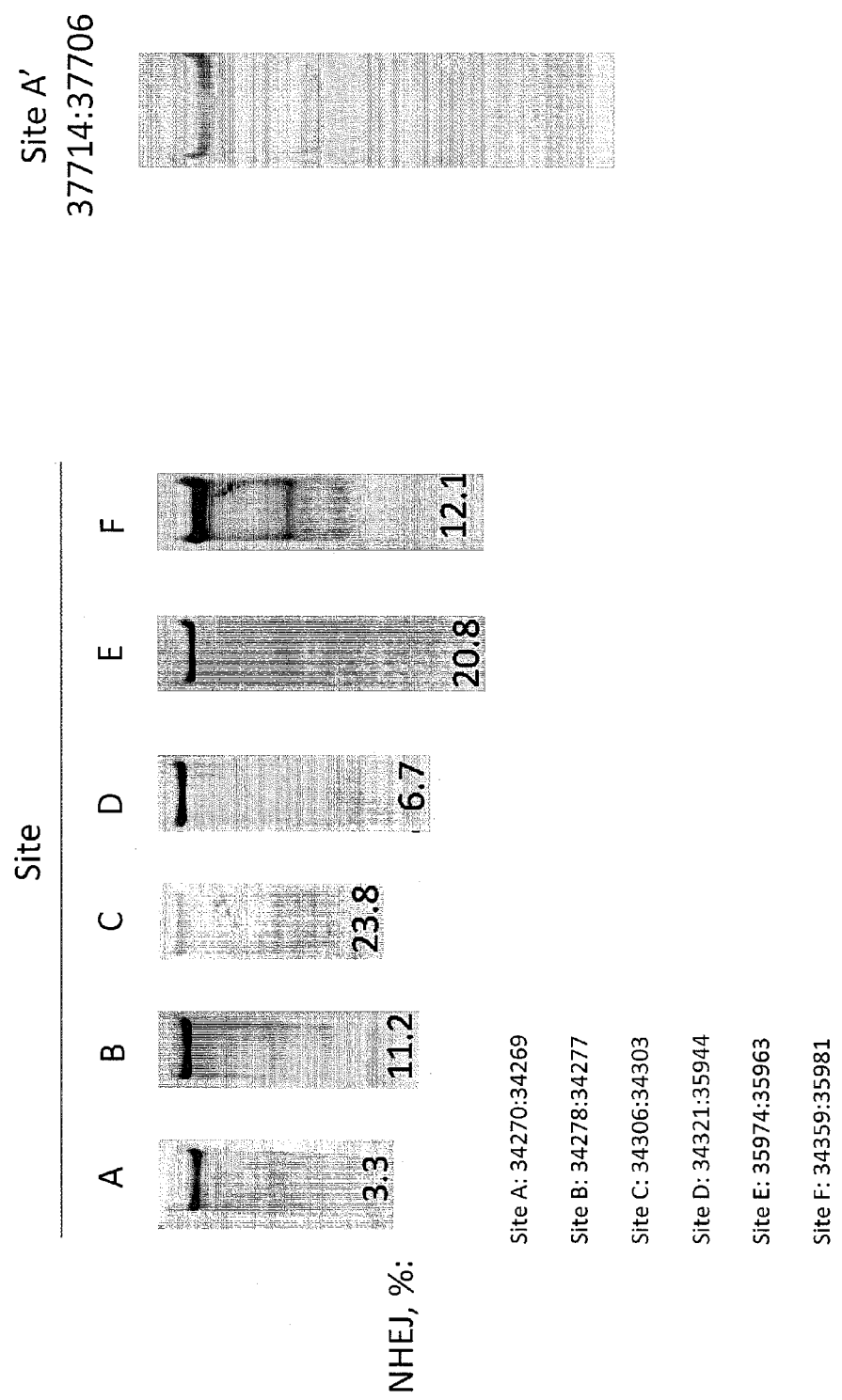
FIG. 12 depicts a series of gels showing the results of a Cel-I mismatch assay on DNA isolated from human CD34+ cells that had been transfected individually with six human HPRT-specific nuclease pairs, each of which cleaves in an intron. "Site" refers to the target site that each ZFN pair cleaves. In addition, an additional ZFN pair ("A'") was tested in K562 cells. The percent of modification detected ("% NHEJ") is shown at the bottom of each lane.

FIG. 12 shows the activity of the seven nuclease pairs with the percentage modification as assayed by the Cel I assay. Thus the ZFN pairs cleaved the HPRT intronic DNA. The oligonucleotides used for PCR for CEL-I analysis are shown below.

TABLE 8

Intronic HPRT ZFN pairs

| Site | ZFN pair | CEL-I primer, F | CEL-I primer, R |
|---|---|---|---|
| A | 34270:34269 | TGT CCT TGG CCA CAC TGT TA (SEQ ID NO: 151) | GGG AGT AAA ATG ACA TGG CCT A (SEQ ID NO: 152) |
| B | 34278:34277 | ATG CCT TTT GGG AAG AGT TG (SEQ ID NO: 153) | CCA GCC AGA ACT CCT TGA AA (SEQ ID NO: 154) |
| C | 34306:34303 | CTG GCA TAA TCT TTT CCC CC (SEQ ID NO: 155) | TTT GAG GTT TCC AGT GCT GA (SEQ ID NO: 156) |
| D | 34321:35944 | TCA GCA CTG GAA ACC TCA AA (SEQ ID NO: 157) | CCA CGC CTG GTC ACT TTC (SEQ ID NO: 158) |
| E | 35974:35963 | CTC CTT GGC TGA GAG GAG TG (SEQ ID NO: 159) | TTA ACT CTC TTG CCT GGC CT (SEQ ID NO: 160) |
| F | 34359:35981 | CTT GGG GCA AAC AGG AGT AT (SEQ ID NO: 161) | AAA GAA AGA AAA GGC AAC AAG C (SEQ ID NO: 162) |
| A' | 37714:37706 | CTT GGG GCA AAC AGG AGT AT (SEQ ID NO: 163) | AAA GAA AGA AAA GGC AAC AAG C (SEQ ID NO: 164) |

Example 11

Targeted Integration into the Human HPRT Locus in CD34+ Cells

Figure 13:
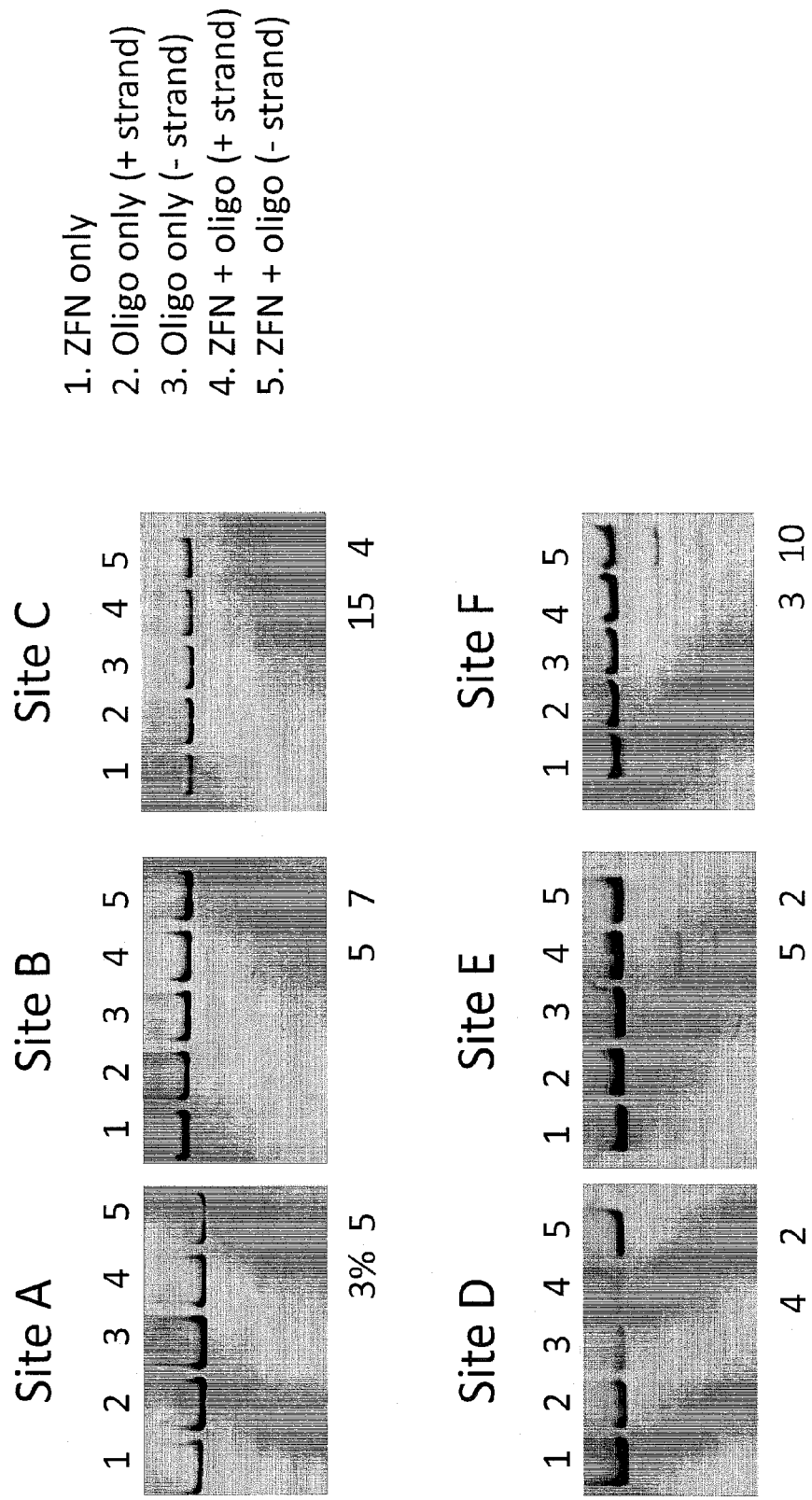
FIG. 13, panels A to F, depict gels showing the targeted integration in CD34+ cells of an oligo donor into each of the six loci cleaved in FIG. 12. The percent of targeted modification detected is shown at the bottom of each lane.
Figure 14:
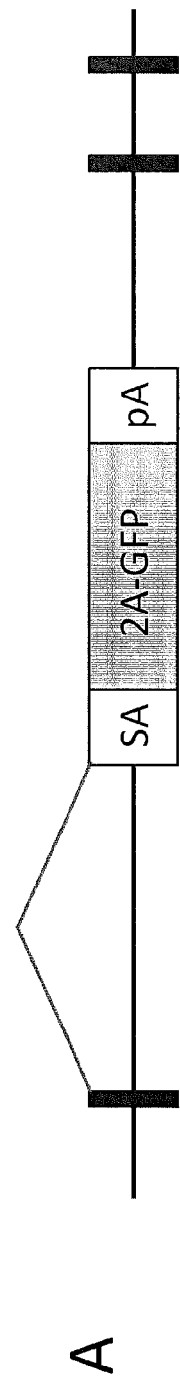
FIG. 14, panels A-C, depict the integration of a SA-2A-GFP-pA transgene into the HPRT locus in human K562 cells.
Figure 14:
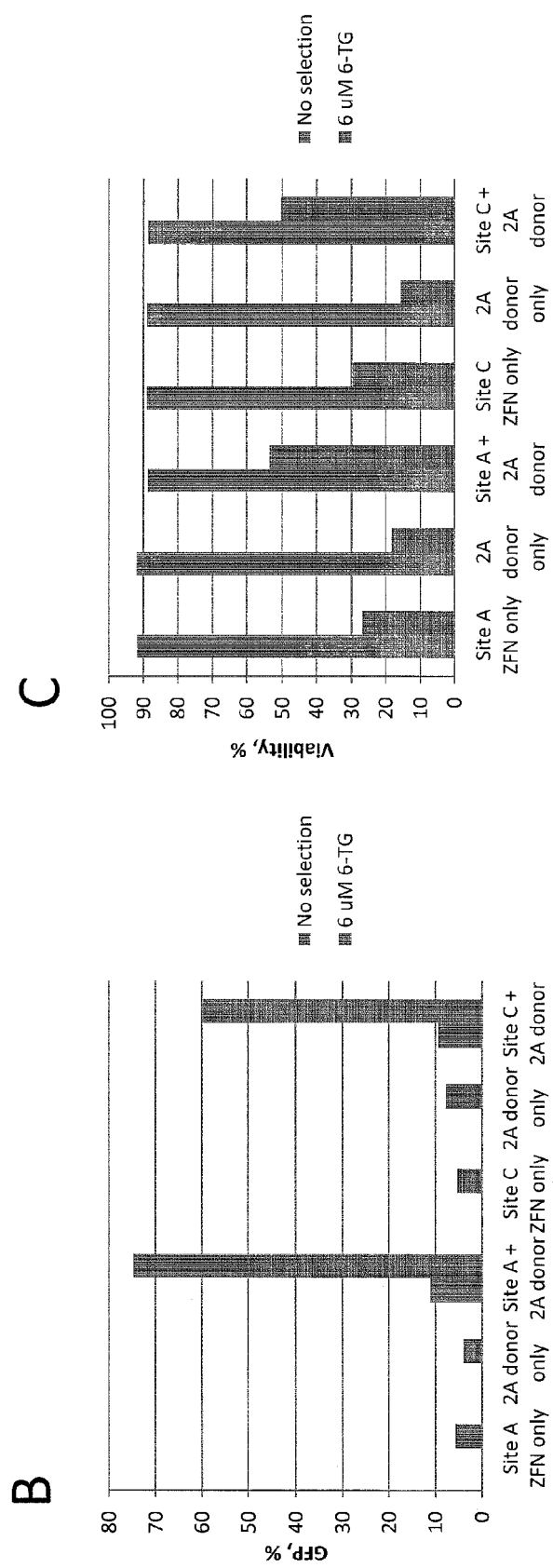

In FIG. 13, an oligonucleotide donor was co-transfected with the indicated ZFN mRNA pairs. PCR products were generated using the oligonucleotides shown in Table 8. Integration of the exogenous DNA sequence into the HPRT intron was assayed by digestion with the restriction enzyme indicated below. We thus demonstrated modification of the human HPRT locus in CD34+ cells. The DNA sequence of the oligonucleotide donors and the restriction enzymes used for detection of targeted integration are shown in Table 9 below. Asterisks indicate phosphorothioate linkages.

TABLE 9

Oligonucleotide donor sequences

| Site | Restriction enzyme | Oligonucleotide donor sequence |
|---|---|---|
| A | KpnI | C*A *CT GTG ACC TGC ATA CTA CAA GTC TAC TTT GTT TTC TAT CCA TTG TTT GTA TCT GGG TAC CTT GCA AAA GGT AGG AAA AGG ACC AAC CAG ATC AGC AGA GAA GAG TTG CCT TGG AGT TTT *C* T (SEQ ID NO: 137) |
| A | KpnI | A*G *AA AAC TCC AAG GCA ACT CTT CTC TGC TGA TCT GGT TGG TCC TTT TCC TAC CTT TTG CAA GGT ACC AGA TCA ACA ATG GAT AGA AAA CAA AGT AGA CTT GTA GTA TGC AGG TCA CAG *T* G (SEQ ID NO: 138) |
| B | SphI | G*C *CA GAA TTC CTG TTT TAG AAT ACA TCT CTG CTG ATC TGT CTG TAT TCT TAG ACT GCA TGC ATC TGG GAT GAA CTC TGG GCA GAA TTC ACA TGG GCT TCC TTT GAA ATA AAC AAG ACT TTT *C* A (SEQ ID NO: 139) |
| B | SphI | T*G *AA AAG TCT TGT TTA TTT CAA AGG AAG CCC ATG TGA ATT CTG CCC AGA GTT CAT CCC AGA TGC ATG CAG TCT AAG AAT ACA GAC AGA TCA GCA GAG ATG TAT TCT AAA ACA GGA ATT CTG *G* C (SEQ ID NO: 140) |
| C | NcoI | G*A *CC AGG GGC ATG TCC TGG TCC ACC TAC CTG AAA ATG TTT GCA ACC AGC CTC CTG GCC ATG GTT GCA CAG GGG CTG AAG TTG TCC CAC AGG TAT TAC GGG CCA ACC TGA CAA TAC ATG AAG *T* T (SEQ ID NO: 141) |
| C | NcoI | A*A *CT TCA TGT ATT GTC AGG TTG GCC CGT AAT ACC TGT GGG ACA ACT TCA GCC CCT GTG CAA CCA TGG CCA GGA GGC TGG TTG CAA ACA TTT TCA GGT AGG TGG ACC AGG ACA TGC CCC TGG *T* C (SEQ ID NO: 142) |
| D | ClaI | T*T *AA TTA TGG TTT GAC CAA TAT TTA TTG GAA ACC GCC AAA GCT TAA ATC ATC AGC TAT CGA TGA ATG TGA TTT GAA AGG TAA TTT AGT ATT GAA TAG CAT GTG AGC TAG AGT ATT TCA T*T *C (SEQ ID NO: 143) |
| D | ClaI | G*A *AT GAA ATA CTC TAG CTC ACA TGC TAT TCA ATA CTA AAT TAC CTT TCA AAT CAC ATT CAT CGA TAG CTG ATG ATT TAA GCT TTG GCG GTT TCC AAT AAA TAT TGG TCA AAC CAT AAT T*A *A (SEQ ID NO: 144) |
| E | PvuII | G*T *GG GAA GCT TGT TCC AGA CAG CCA AGG AGG GAG GTT CGC GCA GTT CCT TTG GCC ACC CAG CTG TGG GGT AAT TGA TCC ATG TAT GCC ATT CAT GTA CAA TGT AGG CAC TTA TAC CTG TAT *T* C (SEQ ID NO: 145) |
| E | PvuII | G*A *AT ACA GGT ATA AGT GCC TAC ATT GTA CAT GAA TGG CAT ACA TGG ATC AAT TAC CCC ACA GCT GGG TGG CCA AAG GAA CTG CGC GAA CCT CCC TCC TTG GCT GTC TGG AAC AAG CTT CCC *A* C (SEQ ID NO: 146) |
| F | HindIII | G*A *CT CCA TAC TTT TCA GTT CTT GAA TAT TTT TTC CTT TAT TCC TCT TGT CTC TGT AAA GCT TAC ATC AAC TGG AGT TGG ACT GTA ATA CCA GGT ATC TCC AGA AGA TGG CAC TAT TTA ACA G*A *T (SEQ ID NO: 147) |
| F | HindIII | A*T *CT GTT AAA TAG TGC CAT CTT CTG GAG ATA CCT GGT ATT ACA GTC AAC TCC AGT TGA TGT AAG CTT TAC AGA GAC AAG AGG AAT AAA AGG AAA AAA TAT TCA AGA ACT GAA AAG TAT GGA G*T *C (SEQ ID NO: 148) |

Example 12

Targeted Integration of a Transgene into the Human HPRT Locus in K562 Cells

Plasmid DNA donors were constructed containing 476 bp of HPRT DNA flanking the site C cleavage site on the 5' and 354 bp of HPRT DNA flanking the cleavage site on the 3'. In between these regions of chromosomal homology was placed a strong splice acceptor sequence (DeKelver et al. (2010) *Genome Research* 20:1133-1142). Similarly, donors were constructed containing 429 bp of HPRT homology on the 5' end, and 616 bp of HPRT homology on the 3' end for the site A cleavage site. Next, in frame with HPRT was placed DNA sequence encoding the viral 2A self cleavage peptide followed by the gene for the green fluorescent protein. The polyadenylation signal from the bovine growth hormone gene was inserted after the transgene coding sequence. This plasmid was co-transfected into K562 cells with mRNA encoding the site C or site A ZFN pair. Cultures were split in half four days post-transfection and 6-TG selection applied to one half of the cells as described above. Culture viability and the percentage of GFP-positive cells were assayed one week after 6-TG selection by Guava-based cell fluorescence measurement according to manufacturer's protocol. The results demonstrate successful integration of the transgene into HPRT and the successful selection of HPRT-negative, transgene-containing cells with 6-TG.

Figure 15:
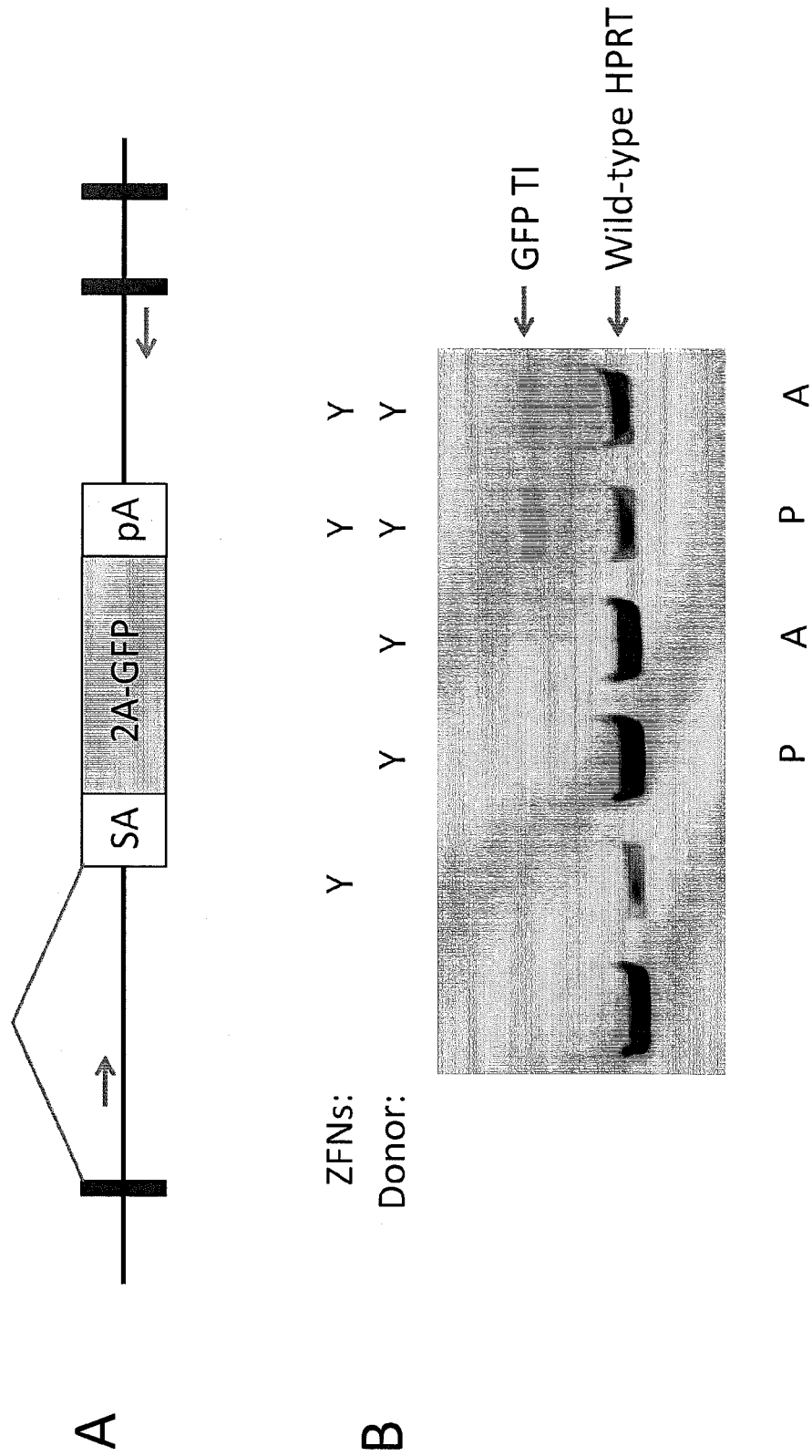
FIG. 15, panels A and B, depict PCR detection of targeted integration of the SA-2A-GFP-pA cassette into HPRT in human K562 cells without 6-TG selection.

Next, the targeted integration into site C was assayed by PCR (FIG. 15). Two systems of donor deliver were tested: delivery from a plasmid (P) as described above, or delivery using a plasmid further containing AAV2 ITRs (A). The HPRT locus was amplified by PCR using the oligonucleotides 5'-AGT ACT CTG GAT CTT CCT GAT T-3' (SEQ ID NO:149) and 5'-CCC ATT CAC CAT TAT ATT CAA AGT C-3' (SEQ ID NO:150). The wild-type HPRT gene gives a 968 bp PCR product; an HPRT allele with the transgene inserted gives a 2076 bp PCR product.

Example 13

Targeted Integration of a Transgene into the Human HPRT Locus in CD34+ Cells

Next, the transgene donor for site C was integrated into HPRT in CD34+ cells. Cells were transfected with the site C ZFNs via Amaxa nucleofection of the encoding mRNAs according to manufacturer's protocol and donor was delivered via the AAV2 plasmid described above.

Figure 16:
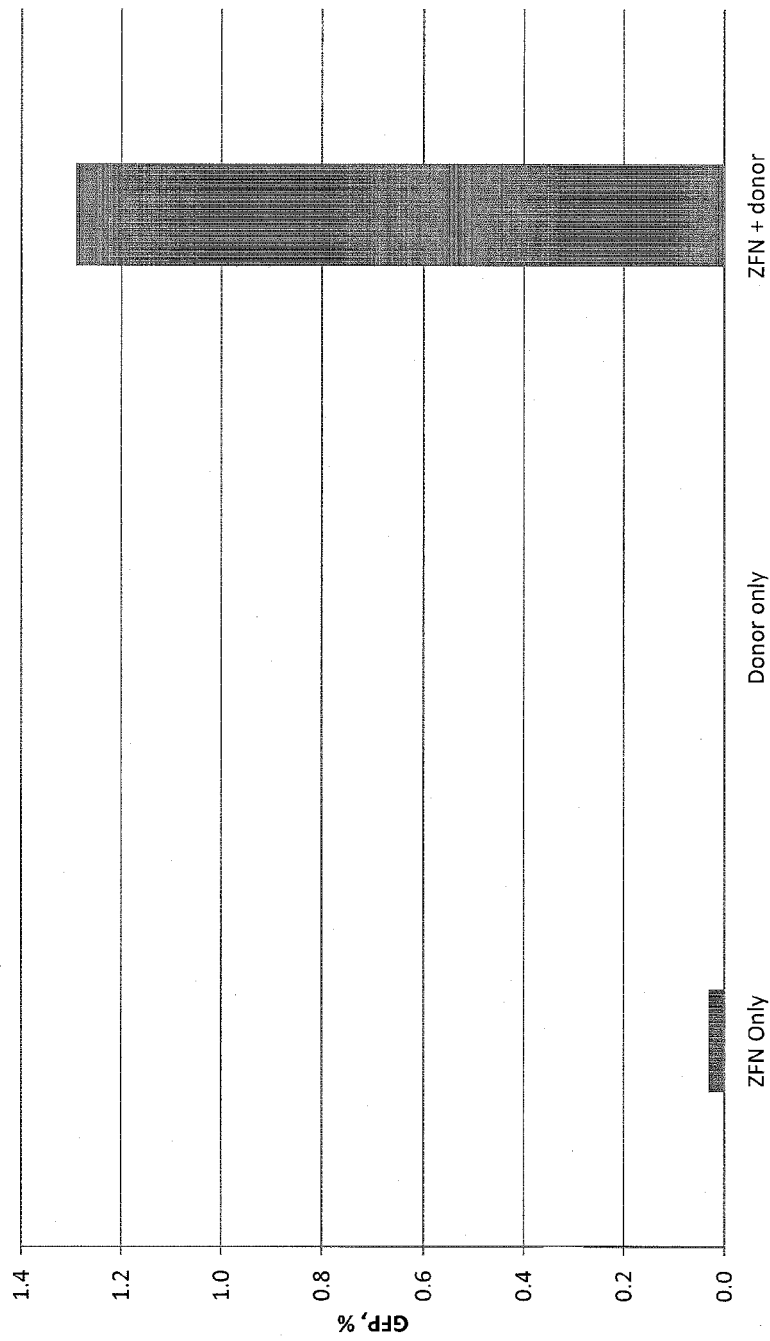
FIG. 16 is a graph depicting integration of the SA-2A-GFP-pA transgene into the HPRT intronic locus in human CD34+ cells. The left-most bar shows the percentage of GFP-positive cells.

As shown in FIG. 16, The number of GFP-positive cells assayed three days later by Guava according to manufacturer's protocols and demonstrated successful targeted integration into CD34+ cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A non-naturally occurring fusion protein comprising a zinc finger protein that binds to an endogenous hypoxanthine-guanine phosphoribosyltransferase (HPRT) gene and a nuclease cleavage domain, wherein the fusion protein modifies the endogenous HPRT gene and further wherein the zinc finger protein comprises 5 or 6 zinc finger domains, each zinc finger domain comprising a recognition helix region, wherein the zinc finger protein comprises the recognition helix regions in the order shown in a single row of rows 3 to 5 or 10 to 23 of Table 1 and further wherein the zinc finger protein targets a sequence selected from the group consisting of SEQ ID NO: 41, 42 or 125-136.

2. An isolated cell comprising one or more fusion proteins according to claim 1.

3. The cell of claim 2, wherein the cell is selected from the group consisting of a T-cell, a B-cell or a stem cell.

4. The cell of claim 3, wherein the stem cell is selected from the group consisting of an embryonic stem cell (ESC), an induced pluripotent stem cell (iPSC), a CD34+ hematopoietic stem cell and a hepatic stem cell.

5. A kit comprising a fusion protein according to claim 1.

6. A cell or cell line in which an endogenous HPRT is partially or fully inactivated using a fusion protein according to claim 1.

7. A polynucleotide encoding one or more fusion proteins of claim 1.

8. An isolated cell comprising one or more polynucleotides according to claim 7.

9. The cell of claim 8, wherein the cell is selected from the group consisting of a T-cell, a B-cell or a stem cell.

10. The cell of claim 9, wherein the stem cell is selected from the group consisting of an embryonic stem cell (ESC), an induced pluripotent stem cell (iPSC), a CD34+ hematopoietic stem cell and a hepatic stem cell.

11. A kit comprising a polynucleotide according to claim 7.

12. A method of cleaving an endogenous HPRT gene in a cell, the method comprising:
introducing, into the cell, one or more polynucleotides according to claim 7, under conditions such that the one or more fusion proteins are expressed and the HPRT gene is cleaved.

13. The method of claim 12, wherein the cell is selected from the group consisting of a T-cell, a B-cell or a stem cell.

14. The method of claim 13, wherein the stem cell is selected from the group consisting of an embryonic stem cell (ESC), an induced pluripotent stem cell (iPSC), a CD34+ hematopoietic stem cell and a hepatic stem cell.

15. A cell or cell line made by the method of claim 12.

16. A method of integrating a transgene into an endogenous HPRT gene, the method comprising,
cleaving an endogenous HPRT gene according to the method of claim 12, in the presence of a transgene, such that the transgene is integrated into the cleaved endogenous HRPT gene of the cell.

17. The method of claim 16, wherein the transgene is introduced to the cell using a viral vector, as an oligonucleotide or on a plasmid.

18. The method of claim 16, wherein the transgene is integrated into the HPRT locus.

19. The method of claim 16, wherein the transgene is under the control of an endogenous promoter.

20. The method of claim 16, wherein the transgene is under the control of an exogenous promoter.

21. A cell or cell line made by the method of claim 16.

22. The method of integrating a transgene into the genome of a cell, the comprising an inactivated HPRT gene, the method comprising inactivating the HPRT gene of the cell by cleaving the endogenous HPRT gene according to the claim 12, and integrating the transgene into a CCR5 gene, a CXCR4 gene, an albumin gene, an AAVS1 gene, a Rosa gene or a beta-globin gene of the cell.

23. A cell or cell line made by the method of claim 22.

24. A method of enriching for cells modified by a nuclease at an endogenous locus, the method comprising:

cleaving an endogenous HPRT gene in a cell according to the method of claim 12;

introducing into the cell, one or more polynucleotides encoding nucleases that cleave the genome of the cell at the endogenous locus;

subjecting the cells to selection with 6-TG, thereby enriching the cells for those in which the endogenous locus has been modified.

25. The method of claim 24, wherein the endogenous locus is inactivated.

26. The method of claim 24, wherein a transgene is integrated into the endogenous locus following cleavage by the nucleases.

27. The method of claim 24, wherein the endogenous locus is selected from the group consisting of HPRT, AAVS1, albumin, beta-globin and Rosa26.

28. The method of claim 24, wherein the cell is selected from the group consisting of a T-cell, a B-cell or a stem cell.

29. The method of claim 28, wherein the stem cell is selected from the group consisting of an embryonic stem cell (ESC), an induced pluripotent stem cell (iPSC), a CD34+ hematopoietic stem cell and a hepatic stem cell.

\* \* \* \* \*

SEQUENCE LISTING

```
<160> NUMBER OF SEQ ID NOS: 167

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp Ala Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Ser Ala Leu Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asn Leu Ser Gln
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Ala Ser Asn Asp Arg Lys Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp Asn Leu Ser Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Asn Asn Asp Arg Lys Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg Ser His Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Thr Leu Ser Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ser Ser His Leu Ala Arg
1               5

<210> SEQ ID NO 10
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Asp Thr Leu Ser Gln
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Arg Gln Ala Arg Ile Gln
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser His Leu Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Gly His Leu Ser Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Asp Ser Leu Ser Val
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Ala Asn Leu Thr Arg
```

```
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Asn Leu Ser Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Arg Arg Ala Leu Ser Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly Ser Leu Thr Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Asn Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Arg Ser Asn Leu Asp Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 21

Arg Ser Asp Asn Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Gln Ser Tyr Arg Arg Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Ala Ala Leu Ala Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp Ser Leu Leu Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Cys Ala Arg Asn Val
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Gly Asn Leu Ala Arg
1               5

<210> SEQ ID NO 27

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ser Thr Pro Arg Asn Lys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Asp Ala Leu Ser Glu
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Asn Ala Thr Arg Thr Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Arg Ser Ala Leu Thr Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Arg Cys Asn Leu Arg Cys
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Asp Arg Ser Ala Leu Ser Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ser Gly Ser Leu Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Asp Asp Leu Thr Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp Asp Arg Lys Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp Ala Leu Thr Gln
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Ser Gly Ser Leu Ser Arg
1               5

<210> SEQ ID NO 38
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 38

Asp Ser Ser Asp Arg Lys Lys
1               5

<210> SEQ ID NO 39
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 39
acccgcagtc ccagcgtcgt ggtgagcc                                        28

<210> SEQ ID NO 40
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 40
gcatgacggg accggtcggc tcgcggca                                        28

<210> SEQ ID NO 41
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 41
tgatgaagga gatgggaggc catcacat                                        28

<210> SEQ ID NO 42
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 42
atctcgagca agacgttcag tcctacag                                        28

<210> SEQ ID NO 43
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 43
aagcactgaa tagaaatagt gatagatc                                        28

<210> SEQ ID NO 44
<211> LENGTH: 28
<212> TYPE: DNA
<213> ORGANISM: Unknown
<220> FEATURE:
```

```
<223> OTHER INFORMATION: Description of Unknown:  Mouse or Human
      HPRT-specific zing finger oligonucleotide

<400> SEQUENCE: 44
atgtaatcca gcaggtcagc aaagaatt                                              28

<210> SEQ ID NO 45
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 45
ggccggcgcg cgggctgact gctcagga                                              28

<210> SEQ ID NO 46
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 46
gctccgttat ggcgacccgc agccctgg                                              28

<210> SEQ ID NO 47
<211> LENGTH: 28
<212> TYPE: DNA
<213> ORGANISM: Homo sapiens

<400> SEQUENCE: 47
gggcagtaac ggcagacttc tcctcagg                                              28

<210> SEQ ID NO 48
<211> LENGTH: 28
<212> TYPE: DNA
<213> ORGANISM: Homo sapiens

<400> SEQUENCE: 48
tggggcaagg tgaacgtgga tgaagttg                                              28

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ser Gly Asp Leu Thr Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Asn Ala Thr Arg Ile Lys
```

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Asp Ser Leu Ser Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ser Ser Asn Arg Lys Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ser Ala Ala Leu Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Leu Asp Asn Arg Thr Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ser Ser His Leu Ser Arg
1               5

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccagaaggtt ttaatccaaa taaggagaag atatg                         35

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aacgatcctg agacttccac actgatgc                                 28

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
agccactggc ccagtttcta cagtctc                                  27

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gacgtgcggc ttccgtttgt c                                        21

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcctcccatc tccttcatca cat                                      23

<210> SEQ ID NO 61
<211> LENGTH: 59
<212> TYPE: DNA
<213> ORGANISM: Canis sp.

<400> SEQUENCE: 61 aactttgtt aaattcctga ttttatttct gtaggactga gcggcttgct cgagatgtg    59

<210> SEQ ID NO 62
<211> LENGTH: 60
<212> TYPE: DNA
<213> ORGANISM: Homo sapiens

<400> SEQUENCE: 62
aactttctat taaattcctg attttatttc tgtaggactg aacgtcttgc tcgagatgtg  60

```
<210> SEQ ID NO 63
<211> LENGTH: 62
<212> TYPE: DNA
<213> ORGANISM: Canis sp.

<400> SEQUENCE: 63
atgaaggaaa tgggaggcca tcacatccgt agcccctctg tgtgctcaag ggaggctata     60
aa                                                                    62

<210> SEQ ID NO 64
<211> LENGTH: 61
<212> TYPE: DNA
<213> ORGANISM: Homo sapiens

<400> SEQUENCE: 64
atgaaggaga tgggaggcca tcacattgta gcccctctgt gtgctcaagg ggggctataa     60
a                                                                     61

<210> SEQ ID NO 65
<211> LENGTH: 60
<212> TYPE: DNA
<213> ORGANISM: Canis sp.

<400> SEQUENCE: 65
ttctttgctg acctgctgga ttatatcaaa gcactgaaca gaaatagtga tggatccatt     60

<210> SEQ ID NO 66
<211> LENGTH: 59
<212> TYPE: DNA
<213> ORGANISM: Homo sapiens

<400> SEQUENCE: 66
ttctttgctg acctctggat tacatcaaag cactgaatag aaatagtgat agatccatt      59

<210> SEQ ID NO 67
<211> LENGTH: 49
<212> TYPE: DNA
<213> ORGANISM: Canis sp.

<400> SEQUENCE: 67
cctatgactg tagatttcat cagactgaag agctactgtg taagtatat                 49

<210> SEQ ID NO 68
<211> LENGTH: 49
<212> TYPE: DNA
<213> ORGANISM: Homo sapiens

<400> SEQUENCE: 68
cctatgactg tagattttat cagactgaag agctattgtg tgagtatat                 49

<210> SEQ ID NO 69
<211> LENGTH: 17
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 69
tggatctatc actattt                                                    17

<210> SEQ ID NO 70
<211> LENGTH: 13
```

```
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 70
tgctcaccac gac                                                        13

<210> SEQ ID NO 71
<211> LENGTH: 14
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 71
tccgttatgg cgac                                                       14

<210> SEQ ID NO 72
<211> LENGTH: 16
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 72
tgggcctgaa ccggcc                                                     16

<210> SEQ ID NO 73
<211> LENGTH: 16
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 73
tggcgtcgtg gtgagc                                                     16

<210> SEQ ID NO 74
<211> LENGTH: 17
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 74
tctatcacta tttctat                                                    17

<210> SEQ ID NO 75
<211> LENGTH: 18
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 75
ttgctgacct gctggatt                                                   18

<210> SEQ ID NO 76
<211> LENGTH: 18
<212> TYPE: DNA
```

```
<213> ORGANISM: Unknown
<220> FEATURE:
<223> OTHER INFORMATION: Description of Unknown:  Mouse or Human
      HPRT-specific zing finger oligonucleotide

<400> SEQUENCE: 76
tttgctgacc tgctggat                                                   18

<210> SEQ ID NO 77
<211> LENGTH: 18
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 77
tgtaggactg aacgtctt                                                   18

<210> SEQ ID NO 78
<211> LENGTH: 16
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 78
tggcctccca tctcct                                                     16

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Ser Gly His Leu Ala Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Arg Val Ala Leu Gln Ala
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Ser Ser His Leu Thr Arg
1               5

<210> SEQ ID NO 82
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Asp Ser Asn Leu Ser Val
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Lys Ile Asn Leu Gln Val
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Asp Val Leu Ser Ala
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Asn Ala Thr Arg Ile Asn
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Ser Gly Asn Leu Thr Arg
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

```
Gln Ser Asn Asp Leu Asn Ser
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Ser Thr Arg Thr Asn
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Ala His Leu Ser Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Lys Val Thr Leu Ala Ala
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Gly Ala Asn Leu Ile Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ser Ser Asp Leu Ser Arg
1               5

<210> SEQ ID NO 93
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 93

Arg Ser Asp His Leu Ser Gln
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Asn Ser Asn Arg Ile Asn
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ser Asp Val Leu Ser Glu
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Asn Gln His Arg Lys Thr
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Arg Ser Asp Leu Ser Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Asp Asn Leu Ser Asn
1               5

```
<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Ser Ser Asn Arg Lys Asn
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Arg Ser Cys Leu Arg Ala
1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Ser Gly Asn Arg Thr Thr
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ser Ser Asn Leu Ser Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Ser Gln Asp Leu Asn Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

```
Asn Asn Arg Asp Leu Ile Asn
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Ser Ser Asn Leu Ser Thr
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

His Ser Asn Ala Arg Lys Thr
1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Ser Gly Ala Leu Ala Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ser Asp His Leu Ser Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Arg Gly Thr Leu Ala Arg
1               5

<210> SEQ ID NO 110
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 110

Arg Ser Asp Ala Leu Ala Arg
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ala Arg Trp Tyr Leu Asp Lys
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Arg Ser Asn Leu Lys Val
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Lys Val Asn Leu Arg Glu
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Arg Thr His Leu Thr Gln
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Arg Ser Pro Leu Arg Asn
1               5
```

```
<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Ser Ser Asn Arg Gln Lys
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ser Asp Asn Leu Ser Val
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Asn Ala Asn Arg Ile Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Leu Lys Gln His Leu Asn Glu
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Asn Ala His Arg Lys Thr
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 121

Asp Ser Ser His Arg Thr Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Thr Arg Asn Arg Trp Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ser Asp His Leu Ser Glu
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

His Ser Arg Thr Arg Thr Lys
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Ala Gly Gln Arg Arg Val
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Arg Ser His Leu Ala Arg
1               5

<210> SEQ ID NO 127
<211> LENGTH: 28
<212> TYPE: DNA
```

```
<213> ORGANISM: Unknown
<220> FEATURE:
<223> OTHER INFORMATION: Description of Unknown: Mouse or Human
      HPRT-specific zing finger oligonucleotide

<400> SEQUENCE: 127
ctgggatgaa ctctgggcag aattcaca                                          28

<210> SEQ ID NO 128
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 128
atgcagtcta agaatacaga cagatcag                                          28

<210> SEQ ID NO 129
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 129
tgcacagggg ctgaagttgt cccacagg                                          28

<210> SEQ ID NO 130
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 130
tggccaggag gctggttgca aacatttt                                          28

<210> SEQ ID NO 131
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 131
ttgaatgtga tttgaaaggt aatttagt                                          28

<210> SEQ ID NO 132
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 132
aagctgatga tttaagcttt ggcggttt                                          28

<210> SEQ ID NO 133
<211> LENGTH: 28
<212> TYPE: DNA
<213> ORGANISM: Unknown
```

```
<220> FEATURE:
<223> OTHER INFORMATION: Description of Unknown: Mouse or Human
      HPRT-specific zing finger oligonucleotide

<400> SEQUENCE: 133
gtggggtaat tgatccatgt atgccatt                                          28

<210> SEQ ID NO 134
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 134
gggtggccaa aggaactgcg cgaacctc                                          28

<210> SEQ ID NO 135
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 135
atcaactgga gttggactgt aataccag                                          28

<210> SEQ ID NO 136
<211> LENGTH: 28
<212> TYPE: DNA
<213> ORGANISM: Unknown
<220> FEATURE:
<223> OTHER INFORMATION: Description of Unknown: Mouse or Human
      HPRT-specific zing finger oligonucleotide

<400> SEQUENCE: 136
ctttacagag acaagaggaa taaaggaa                                          28

<210> SEQ ID NO 137
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 137
cactgtgacc tgcatactac aagtctactt tgttttctat ccattgtttg tatctgggta       60
ccttgcaaaa ggtaggaaaa ggaccaacca gatcagcaga gaagagttgc cttggagttt     120
tct                                                                   123

<210> SEQ ID NO 138
<211> LENGTH: 123
<212> TYPE: DNA
<213> ORGANISM: Artificial Sequence
<220> FEATURE:
<223> OTHER INFORMATION: Description of Artificial Sequence: Synthetic
```

-continued

```
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 138
agaaaactcc aaggcaactc ttctctgctg atctggttgg tcctttcct accttttgca      60 aggtacccag atacaaacaa tggatagaaa acaaagtaga cttgtagtat gcaggtcaca    120
gtg                                                                  123

<210> SEQ ID NO 139
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 139
gccagaattc ctgttttaga atacatctct gctgatctgt ctgtattctt agactgcatg     60
catctgggat gaactctggg cagaattcac atgggcttcc tttgaaataa acaagacttt   120
tca                                                                  123

<210> SEQ ID NO 140
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 140
tgaaaagtct tgtttatttc aaaggaagcc catgtgaatt ctgcccagag ttcatcccag     60
atgcatgcag tctaagaata cagacagatc agcagagatg tattctaaaa caggaattct   120
ggc                                                                  123

<210> SEQ ID NO 141
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
```

```
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 141
gaccaggggc atgtcctggt ccacctacct gaaaatgttt gcaaccagcc tcctggccat     60
ggttgcacag gggctgaagt tgtcccacag gtattacggg ccaacctgac aatacatgaa   120
gtt                                                                  123

<210> SEQ ID NO 142
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 142
aacttcatgt attgtcaggt tggcccgtaa tacctgtggg acaacttcag ccctgtgca     60 accatggcca ggaggctggt tgcaaacatt ttcaggtagg tggaccagga catgcccctg   120
gtc                                                                  123

<210> SEQ ID NO 143
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (119)..(121)
<223> OTHER INFORMATION: Phosphorothioate linkages

<400> SEQUENCE: 143
ttaattatgg tttgaccaat atttattgga aaccgccaaa gcttaaatca tcagctatcg     60
atgaatgtga tttgaaaggt aatttagtat tgaatagcat gtgagctaga gtatttcatt   120
c                                                                    121

<210> SEQ ID NO 144
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (119)..(121)
```

<223> OTHER INFORMATION: Phosphorothioate linkages

<400> SEQUENCE: 144
gaatgaaata ctctagctca catgctattc aatactaaat tacctttcaa atcacattca    60
tcgatagctg atgatttaag ctttggcggt ttccaataaa tattggtcaa accataatta   120
a                                                                   121

<210> SEQ ID NO 145
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 145
gtgggaagct tgttccagac agccaaggag ggaggttcgc gcagttcctt tggccaccca    60
gctgtggggt aattgatcca tgtatgccat tcatgtacaa tgtaggcact tatacctgta   120
ttc                                                                 123

<210> SEQ ID NO 146
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (121)..(123)
<223> OTHER INFORMATION: Phosphorothioate linkages

<400> SEQUENCE: 146
gaatacaggt ataagtgcct acattgtaca tgaatggcat acatggatca attacccac     60 agctgggtgg ccaaaggaac tgcgcgaacc tccctccttg gctgtctgga acaagcttcc   120
cac                                                                 123

<210> SEQ ID NO 147
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (122)..(124)
<223> OTHER INFORMATION: Phosphorothioate linkages

<400> SEQUENCE: 147

```
gactccatac ttttcagttc ttgaatattt tttcctttat tcctcttgtc tctgtaaagc    60
ttacatcaac tggagttgga ctgtaatacc aggtatctcc agaagatggc actatttaac   120
agat                                                                124

<210> SEQ ID NO 148
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (122)..(124)
<223> OTHER INFORMATION: Phosphorothioate linkages

<400> SEQUENCE: 148
atctgttaaa tagtgccatc ttctggagat acctggtatt acagtccaac tccagttgat    60
gtaagcttta cagagacaag aggaataaag gaaaaaatat tcaagaactg aaaagtatgg   120
agtc                                                                124

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agtactctgg atcttcctga tt                                             22

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cccattcacc attatattca aagtc                                          25

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tgtccttggc cacactgtta                                                20

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 152
gggagtaaaa tgacatggcc ta                                              22

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
atgccttttg ggaagagttg                                                 20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ccagccagaa ctccttgaaa                                                 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ctggcataat cttttccccc                                                 20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
tttgaggttt ccagtgctga                                                 20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tcagcactgg aaacctcaaa                                                 20

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
```

```
ccacgcctgg tcactttc                                                   18
```

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159

```
ctccttggct gagaggagtg                                                 20
```

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160

```
ttaactctct tgcctggcct                                                 20
```

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161

```
cttggggcaa acaggagtat                                                 20
```

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162

```
aaagaaagaa aaggcaacaa gc                                              22
```

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163

```
cttggggcaa acaggagtat                                                 20
```

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164

```
aaagaaagaa aaggcaacaa gc                                              22

<210> SEQ ID NO 165
<211> LENGTH: 9
<212> TYPE: PRT
<213> ORGANISM: Unknown
<220> FEATURE:
<223> OTHER INFORMATION: Description of Unknown: "LAGLIDADG"
      family peptide motif sequence

<400> SEQUENCE: 165

Leu Ala Gly Leu Ile Asp Ala Asp Gly
1               5

<210> SEQ ID NO 166
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 166
tgcaaaaggt aggaaaagga ccaaccag                                        28

<210> SEQ ID NO 167
<211> LENGTH: 28
<212> TYPE: DNA
<213> ORGANISM: Unknown
<220> FEATURE:
<223> OTHER INFORMATION: Description of Unknown:  Mouse or Human
      HPRT-specific zing finger oligonucleotide

<400> SEQUENCE: 167
acccagatac aaacaatgga tagaaaac                                        28
```